(12) United States Patent
Salomon et al.

(10) Patent No.: US 10,087,241 B2
(45) Date of Patent: Oct. 2, 2018

(54) POLYPEPTDES, CELLS, AND METHODS FOR BIOFILM THERAPY AND DETECTION

(71) Applicant: REGENTS OF THE UNIVERSITY OF MINNESOTA, Minneapolis, MN (US)

(72) Inventors: Christine Elizabeth Salomon, Minneapolis, MN (US); Joshua D. Erickson, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/080,254

(22) Filed: Mar. 24, 2016

(65) Prior Publication Data
US 2016/0280772 A1    Sep. 29, 2016

Related U.S. Application Data

(60) Provisional application No. 62/138,774, filed on Mar. 26, 2015.

(51) Int. Cl.
| | | |
|---|---|---|
| *C07K 16/00* | (2006.01) | |
| *C07K 16/12* | (2006.01) | |
| *A01N 63/00* | (2006.01) | |
| *C07K 14/335* | (2006.01) | |

(52) U.S. Cl.
CPC .......... *C07K 16/1214* (2013.01); *A01N 63/00* (2013.01); *C07K 14/335* (2013.01); *C07K 2317/622* (2013.01); *C07K 2317/76* (2013.01); *C07K 2319/30* (2013.01)

(58) Field of Classification Search
CPC ................................................ C07K 16/1214
See application file for complete search history.

(56) References Cited

U.S. PATENT DOCUMENTS

| | | | |
|---|---|---|---|
| 8,153,119 B2 | 4/2012 | Collins | |
| 2002/0044926 A1* | 4/2002 | Reid | A61K 35/745 424/93.45 |
| 2010/0159563 A1* | 6/2010 | Manyak | A61L 2/186 435/201 |

OTHER PUBLICATIONS

Martin et al (Applied and Environmental Microbiology vol. 77, No. 6, pp. 2174-2179, 2011).*
Pier et al (Journal of Immunology vol. 173, pp. 5671-5678, 2004).*
Alipour, "Importance of DNase and alginate lyase for enhancing free and liposome encapsulated aminoglycoside activity against *Pseudomonas aeruginosa*" Aug. 2009m *J Antimicrob Chemother.*, 64(2):317-25. doi: 10.1093/jac/dkp165. Epub May 22, 2009.
Alkawash, "Alginate lyase enhances antibiotic killing of mucoid *Pseudomonas aeruginosa* in biofilms" Feb. 2006, *APMIS*, 114(2):131-8.
Allesen-Holm, "Characterization of DNA release in *Pseudomonas aeruginosa* cultures and biofilms" Feb. 2006 *Mol. Microbiology*, 59(4): 1114-1128.
Aloush, "Multidrug-resistant *Pseudomonas aeruginosa:* risk factors and clinical impact" Jan. 2006 *Antimicrob. Agents Chemother.*, 50(1):43-48.
Anderl, "Role of antibiotic penetration limitation in *Klebsiella pneumoniae* biofilm resistance to ampicillin and ciprofloxacin" Jul. 2000 *Antimicrob. Agents Chemotherapy*, 44(7):1818-1824.
Aslam, Treatment of *Clostridium difficile* associated disease: old therapies and new strategies. Sep. 2005 *Lancet. Infect Dis.*, 5(9):549-557.
Aukrust, Transformation of *Lactobacillus* by Electroporation. In Electroporation Protocols for Microorganisms, J.A. Nickoloff, ed. 1995, Humana Press, pp. 201-208.
Bales, "Purification and Characterization of Biofilm-Associated EPS Exopolysaccharides from ESKAPE Organisms and Other Pathogens" Jun. 2013 *PLoS ONE*, 8(6):e67950.
Bird, Transport Phenomena, 2nd edition. 2002. John Wiley and Sons, New York.
Boucher, "10x'20 Progress—Development of New Drugs Active Against Gram-Negative Bacilli: An Update From the Infectious Diseases Society of America" Jun. 2013 *Clin. Infect. Disease*, 56(12):1685-1694.
Buckingham-Meyer, "Comparative evaluation of biofilm disinfectant efficacy tests" Aug. 2007 *J of Micro. Methods*, 70(2):236-244.
Call, Relevance and application of sortase and sortase-dependent proteins in lactic acid bacteria. 2013 *Front. Micro.*, 4(73): 1-10.
Caso, "Detection and analysis of extra- and intracellular deoxyribonuclease activities in *Lactobacillus plantarum*" Aug. 1997 *L App Micro*, 25(2):148-152.
Callura, "Tracking, tuning, and terminating microbial physiology using synthetic riboregulators" Sep. 2010 *PNAS*, 107(36):15898-903.
CDC, Center for Disease Control. 2013. Antibiotic resistant threats in the United States.
Ceri, "The Calgary Biofilm Device: new technology for rapid determination of antibiotic susceptibilities of bacterial biofilms" Jun. 1999 *J Clin Microbiol.*, 37(6): 1771-6.
Characklis, Laboratory biofilm reactors. In Biofilms, pp. 55-89. Edited by W.G. Characklis & K.C. Marshall. 1990. New York, NY: John Wiley & Sons, Inc.
Cheema, "The diffusion characteristics of antibiotics in mucus glycoprotein gels" Dec. 1986 *J. Phar. Pharmacol. Suppl.*, 38(S12):53P.
Choi, "Enhanced wound healing by recombinant *Escherichia coli* Nissle 1917 via human epidermal growth factor receptor in human intestinal epithelial cells: therapeutic implication using recombinant probiotics" Mar. 2012 *Infect. Immun.*, 80(3):1079-1087.

(Continued)

*Primary Examiner* — Albert M Navarro
(74) *Attorney, Agent, or Firm* — Mueting, Raasch & Gebhardt, PA

(57) ABSTRACT

This disclosure describes a fusion polypeptide that includes an anchor domain and a binding domain that specifically binds to a target biofilm. The anchor domain generally includes at least a portion of a cell membrane polypeptide. The binding domain includes a sufficient portion of a polypeptide that specifically binds to a component of a target biofilm to specifically bind to the target biofilm. This disclosure also describes cells that include the fusion polypeptide and methods involving the use of such cells.

4 Claims, 10 Drawing Sheets

Specification includes a Sequence Listing.

(56) References Cited

OTHER PUBLICATIONS

Cortes-Perez, "Cell-surface display of E7 antigen from human papillomavirus type-16 in *Lactococcus lactis* and in *Lactobacillus plantarum* using a new cell-wall anchor from *Lactobacilli*" Feb. 2005 *J Drug Target*, 13(2):89-98.
Cunningham, Biofilms: The hypertextbook. Center for Biofilm Engineering, 2005 Montana State University. Online: http://www.hypertextbookshop.com/biofilmbook/v004/r003/index.html.
Darouiche, "Treatment of infections associated with surgical implants" Apr. 2004 *N. Engl. J. Med.*, 350:1422-1429.
Del Pozo, "The Challenge of Treating Biofilm-associated Bacterial Infections" Aug. 2007 *Clin. Pharmacol Ther.*, 82(2):204-209.
Desmond, "Improved Stress Tolerance of GroESL-Overproducing *Lactococcus lactis* and Probiotic *Lactobacillus paracasei* NFBC 3" Oct. 2004 *Appl Environ Microbiol.*, 70(10):5929-5936.
Donati, "Material Properties of Alginates" In Alginates: Biology and Applications B.H.A. Rehm, ed. (Springer Berlin Heidelberg), 2009, pp. 1-53.
Donlan, "Biofilms: microbial life on surfaces" Sep. 2002 *Emerg. Infect. Dis.*, 8(9):881-890.
Donlan, "Biofilms: Survival mechanisms of clinically relevant microorganisms" Apr. 2002 *Clin. Microbiol. Rev.*, 15(2):167-193.
Duan, "Engineered bacterial communication prevents *Vibrio holera* virulence in an infant mouse model" Jun. 2010 *PNAS*, 107(25): 11260-11264.
EPA MB-20-01. Standard Operating Procedure for Single Tube Method for Measuring Disinfectant Efficacy Against Biofilm Grown in the CDC Biofilm Reactor. 2013.
EPA MB-19-02. Standard Operating Procedure for Growing a Pseudomonas aeruginosa biofilm using the CDC Biofilm Reactor. 2013.
Erickson, "Development of Novel Tools to Study and Combat Microbial Biofilms" Presentation Sep. 10, 2014.
Food and Drug Administration (FDA). Generally Recognized as Safe (GRAS). Retrieved 2014. Oline: http://www.fda.gov/Food/IngredientsPackagingLabeling/GRAS/SCOGS/ucm084142.htm.
Flemming, "The EPS Matrix: The 'House of Biofilm Cells'" Nov. 2007 *J Bacteriol.*, 189(22):7945-7947.
Forbes, "Engineering the perfect (bacterial) cancer therapy" Nov. 2010 *Nature Reviews Cancer*, 10(11):785-794.
Franklin, "Biosynthesis of the *Pseudomonas* extracellular polysaccharides, alginate, Pel, and Psl" Aug. 2011 *Front. Microbiology*, 2(167): 1-16.
Fredriksen, "Cell Wall Anchoring of the 37-Kilodalton Oncofetal Antigen by *Lactobacillus plantarum* for Mucosal Cancer Vaccine Delivery" Nov. 2010 *Appl. Environ. Micro.*, 76(21):7359-7362.
Furukawa, "Keeping Their Options Open: Acute versus Persistent Infections" Feb. 2006 *J. Bacteriol.* 188(4):1211-1217.
Gan, "*Lactobacillus fermentum* RC-14 Inhibits *Staphylococcus aureus* Infection of Surgical Implants in Rats" May 2002 *J of Infectious Disease*, 185:1369-72.
Goeres, "Design of Model Reactor Systems for Evaluating Disinfectants against Biofilm Bacteria" Dissertation—Montana State University. Bozeman, Montana, 2006, 92 pages.
Goeres, "A method for growing a biofilm under low shear at the air—liquid interface using the drip flow biofilm reactor" Apr. 2009 *Nature Protocols*, 4:783-788.
Gordon, "Antibiotic interaction and diffusion through alginate and exopolysaccharide of cystic fibrosis-derived Pseudomonas aeruginosa" Nov. 1988 *J. Antimicrob. Chemother.*, 22(5):667-674.
Grobe, "Characterization of mucoid Pseudomonas aeruginosa isolated from technical water systems" Jul. 1995 *J of Appl Bacteriology*, 79(1):94-102.
Hill, "Antibiotic Susceptibilities of Pseudomonas aeruginosa Isolates Derived from Patients with Cystic Fibrosis under Aerobic, Anaerobic, and Biofilm Conditions" Oct. 2005 *J Clin Microbiol.*, 43(10):5085-5090.
Hillman, "Genetically modified *Streptococcus mutans* for the prevention of dental caries" Aug. 2002 *Antonie Van Leeuwenhoek*, 82(1-4):361-366.
Hoffmann, "Novel Mouse Model of Chronic Pseudomonas aeruginosa Lung Infection Mimicking Cystic Fibrosis" Apr. 2005 *Infect. Immun.*, 73(4):2504-2514.
Hostacká, "Temperature and pH affect the production of bacterial biofilm" Jan. 2010 *Folia Microbiol.*, (Praha) 55(1):75-78.
Jean, "Bacterial Delivery of *Staphylococcus aureus* α-Hemolysin Causes Regression and Necrosis in Murine Tumors" Jul. 2014 *Molecular Therapy*, 22(7): 1266-1274.
Jena, "Redirecting T-cell specificity by introducing a tumor-specific chimeric antigen receptor" Aug. 2010 *Blood*, 116(7):1035-1044.
Jensen, "The immune system vs. Pseudomonas aeruginosa biofilms" Aug. 2010 *FEMS Immunol Med Microbiol*, 59(3): 292-305.
Kadurugamuwa, "Bioluminescent imaging of bacterial biofilm infections in vivo" 2008 *Methods Mol. Biol.*, 431:225-239.
Keen, "Phage Therapy: Concept to Cure" 2012 *Front Microbiol.*, 3:238.
Khalil, "Synthetic Biology: Applications Come of Age" May 2010 *Nat Rev Genet.*, 11(5):367-379.
Kharazmi, "Robbins device in biofilm research" In Methods in Enzymology, edited by R.J. Doyle. San Diego, CA: Academic Press. 1999. vol. 310:207-215.
Kleerebezem, "Complete genome sequence of Lactobacillus plantarum WCFS1" Feb. 2003 *PNAS*, 100(4):1990-1995.
Knutson, "A new modification of the carbazole analysis: Application to heteropolysaccharides" 1968 *Analytical Biochemistry* 24:470-481.
Lagenaur, "Prevention of vaginal SHIV transmission in macaques by a live recombinant Lactobacillus" Nov. 2011 *Mucosol Immuno.* 4(6):648-57.
LeBeaux, "From in vitro to in vivo Models of Bacterial Biofilm-Related Infections" 2013 *Pathogens*, 2(2):288-356.
Lennox, Ed. "Biofilms: The Hypertextbook" 2008. Cover page and table of contents. Online: http://biofilmbook.hypertextbookshop.com/public_version.
Lewis, "Assessment of Microbial Biofilm Growth on Nanocrystalline Diamond in a Continuous Perfusion Environment" Jun. 2010 *J. Manuf. Sci. Eng.*, 132(3):030919-030919.
Linker, "A Polysaccharide resembling Alginic Acid from a Pseudomonas Micro-organism" Oct. 1964 *Nature*, 204:187-188.
Lipowska-Bhalla, "Immunotherapy of cancer with CAR T cells: achievements and challenges" 2012 *Cancer Immunol Immunother.*, 61:953-962.
Lu, "Dispersing biofilms with engineered enzymatic bacteriophage" 2007 *PNAS*, 104(27):11197-11202.
Luppens, "Development of a Standard Test to Assess the Resistance of *Staphylococcus aureus* Biofilm Cells to Disinfectants" Sep. 2002 *Appl Environ Microbiol.*, 68(9):4194-4200.
Mah, "Mechanisms of biofilm resistance to antimicrobial agents" Jan. 2001 *TRENDS in Micro.*, 9(1):34-38.
Mann, "Pseudomonas biofilm matrix composition and niche biology" Jul. 2012 *FEMS Microbiol Rev.*, 36(4):893-916.
Matsuzaki, "Modulating immune responses with probiotic bacteria" Feb. 2000 *Immunol Cell Biol.*, 78(1)67-73.
McCue, *In a Page: Infectious disease*, Lippincott Williams & Wilkins: Alphen aan den Rijn, Netherlands 2006. Cover page, title page and table of contents.
Mierau, "10 years of the nisin-controlled gene expression system (NICE) in Lactococcus lactis" Oct. 2005 *Appl Microbiol Biotechnol.*, 68(6)705-717.
Misagh, "Importance of Dnase and alginate lyase for enhancing free and liposomal encapsulated aminoglycoside activity against *Pseudomonas 6eruginosa*" 2009. J. of Anti. Chemo., 64(2):317-325.
Munos, "Lessons from 60 years of pharmaceutical innovation" Dec. 2009 *Nature Rev Drugs Discovery*, 8:959-968.
Nickel, "Tobramycin resistance of *Pseudomonas aeruginosa* cells growing as a biofilm on urinary tract catheter" Apr. 1985 *Antimicrob. Agents Chemother.*, 27(4):619-624.

(56) References Cited

OTHER PUBLICATIONS

National Institutes of Health (NIH). 1999. SBIR/STTR Study and control of microbial biofilms (PA-99-084). http://grants.nih.gov/grants/guide/pa-files/PA-99-084.html. Published Apr. 21, 1999.
National Institutes of Health (NIH). 1998. Targeted research on oral microbial biofilms (DE-98-006). http://grants.nih.gov/grants/guide/rfa-files/RFA-DE-98-006.html. Published Mar. 6, 1998.
Okabe, *Anaerobic SRB biofilms in industrial water systems: a process analysis. In: Biofouling and Biocorrosion in industrial water systems* Lewis Publishers, Boca Rapton, 1994. Chapter 12, pp. 189-204.
Okuda, "Translocation of *Pseudomonas aeruginosa* from the Intestinal Tract is Mediated by the binding of ExoS to the Na.K-ATPase Regulator, FXYD3" Nov. 2010 *Infection and Immunity*, 78(11): 4511-4522.
Olle, "Medicines from microbiota" Apr. 2013 *Nat Biotech.*, 31(4):309-315.
O'Toole, "Microtiter Dish Biofilm Formation Assay" 2011 *J. Vis. Exp.* (47), e2437, doi:10.3791/2437. Complete video online: https://www.ncbi.nlm.nih.gov/pmc/articles/PMC3182663/.
O'Toole, "Initiation of biofilm formation in Pseudomonas fluorescens WCS365 proceeds via multiple, convergent signalling pathways: a genetic analysis" May 1998 *Mol Microbiol.*, 28(3):449-61.
Overkamp, "Benchmarking various GFP variants in *Bacillus subtilis Streptococcus pneumonia,* and *Lactococcus lactis* for live cell imaging" Oct. 2013 *American Society for Microbiology,* 79(20):6481-6490.
PACE, Biofilms, Infection, and Antimicrobial Therapy, CRC Press: Abingdon, England. 2005. Cover page, title page and table of contents.
Parshionikar, 2009. Method Validation of U.S. Environmental Protection Agency Microbiological Methods of Analysis. http://www.epa.gov/fem/pdfs/final_microbiology_method_guidance_110409.pdf.
Peral, M.C., Martinez, M.A.H., and Valdez, J.C. 2009. Bacteriotherapy with 70 *Lactobacillus plantarum* in burns. International Wound Journal 6, 73-81.
Pereira, "Effect of flow regime on the architecture of a *Pseudomonas fluorescens* biofilm" Feb. 2002 *Biotechnol. Bioeng.,* 78(2):164-171.
Pier, "Human Monoclonal Antibodies to *Pseudomonas aeruginosa* Alginate That Protect against Infection by Both Mucoid and Nonmucoid strains" 2004 *J. Immunol.,* 173:5671-8.
Prosser, "Method of evaluating effects of antibiotics on bacterial biofilm" Oct. 1987 *Antimicrob. Agents Chemother.,* 31(10):1502-1506.
Public Law 112-144—Jul. 9, 2012 126. STAT. 993. 112$^{th}$ Congress. Generating Antibiotic Incentives Now (GAIN)—Title VIII. http://www.gpo.gov/fdsys/pkg/PLAW-112publ144/pdf/PLAW-112publ144.pdf.
Quan, "A two-year randomized, placebo-controlled trial of dornase alfa in young patients with cystic fibrosis with mild lung function abnormalities" Dec. 2001 *J. of Pediatrics,* 139(6):813-20.
Rader, "Phage display of combinatorial antibody libraries" Aug. 1997 *Current Opinion in Biotechnology,* 8(4):503-508.
Ramos, "Antipathogenic properties of *Lactobacillus plantarum* on *Pseudomonas aeruginosa:* the potential use of its supernatants in the treatment of infected chronic wounds" 2012 *Wound Repair Regen.,* 20:552-562.
Reid, "Use of *Lactobacillus* to prevent infection by pathogenic bacteria" 2002 *Microbes Infect.,* 4:319-324.
Remus, "Impact of *Lactobacillus plantarum* Sortase on Target Protein Sorting, Gastrointestinal Persistence, and Host Immune Response Modulation" Feb. 2013 *J. Bacteriol.,* 195(3):502-509.
Robinson, *Methods in biotechnology—immobilization of enzymes and cells,* Edited by G F Bickerstaff. Humana Press: New Jersey, NJ 1996. Biochem. Educ., 25(4):232-232.
Saeidi, "Engineering microbes to sense and eradicate *Pseudomonas aeruginosa,* a human pathogen" 2011 *Mol Syst Biol.,* 7:521.

Sambrook, *Molecular Cloning: A Laboratory Manual 3$^{rd}$ edition,* CSHL Press: Cold Spring Harbor, New York. 2001. Cover page, title page and table of contents.
Sauer, "*Pseudomonas aeruginosa* displays multiple phenotypes during development as a biofilm" 2002 *J. Bacteriol.,* 184(4):1140-1154.
Scott, The Direct Medical Costs of Healthcare-associated Infection in U.S. Hospitals and the Benefits of Prevention. Centers for Disease Control. 2009.
Shen, "Engineering Peptide Linkers for scFv Immunosensors" 2008 *Anal Chem.,* 80:1910-1917.
Simsek, "Immobilization of nisin producer *Lactococcus lactis* strains to chitin with surface-displayed chitin-binding domain" May 2013 *Applied Microbiology and Biotechnology,* 97(10):4577-87.
Smith, "Filamentous fusion phage: novel expression vectors that display cloned antigens on the virion surface" 1985 *Science,* 228:1315-1317.
Smith, "Efficacy of common hospital biocides with biofilms of multi-drug resistant clinical isolates" Aug. 2008 *J. Med. Microbiol.* 57:966-973.
Smith, "Activity of Pyocin S2 against *Pseudomonas aeruginosa* Biofilms" Mar. 2012 *Antimicrob. Agents Chemother.,* 56(3):1599-1601.
Steidler, "Therapeutic Drug Delivery by Genetically Modified *Lactococcus lactis*" Aug. 2006 *Annals of the New York Academy of Sciences* 1072:176-186.
Stewart, "Mechanisms of antibiotic resistance in bacterial biofilms" 2002 *Int. J. Med. Microbiol.,* 292:107-113.
Stewart, "Biofilm penetration and disinfection efficacy of alkaline hypochlorite and chlorosulfamates" 2001 *J. Appl. Microbiol.* 91(3):525-532.
Stoodley, "Use of flow cells and annular reactors to study biofilms," in *Biofilms in Industry, Medicine and Environmental Biotechnology.* Lens (Ed.) IWA Publishing: London 2003. Cover page, publisher's page, and pp. 197-213.
Valdéz, Interference of *Lactobacillus plantarum* with *Pseudomonas aeruginosa* in vitro and in infected burns: the potential use of probiotics in wound treatment. 2005.Clin Microbiol Infect11,472-479.
Van Bloois, "Decorating microbes: surface display of proteins on *Escherichia coli*" Feb. 2011 *Trends Biotechnol.,* 29(2):79-86.
Wang, "Immobilization of Cells with Surface-Displayed Chitin Binding Domain" Jan. 2006 *Appl. Environ. Microbiol.,* 72(1):927-931.
Wang, "Synthetic Biology: Advancing the Design of Diverse Genetic Systems" Feb. 2013 *Annual Review of Chemical and Biomolecular Engineering,* 4:69-102.
Wells, "Immunomodulatory mechanisms of *Lactobacilli*" Aug. 2011 *Microbial Cell Factories,* 10(S17): 1-15.
Wernerus, "Biotechnological applications for surface engineered bacteria" Dec. 2004 *Biotechnol. Appl. Biochem.,* 40(Pt3):209-228.
Wingender, "Isolation and biochemical characterization of extracellular polymeric substances from Pseudomonas aeruginosa" 2001 *Meth. Enzymol.,* 336:302-314.
World Health Organization (WHO). "Antimicrobial Resistance: Global guidelines on the prevention of surgical site infection" 2014. Online: http://www.who.int/drugresistance/en/.
Yu "A direct viable count method for the enumeration of attached bacteria and assessment of biofilm disinfection" Apr. 1993 J Microbiol. Methods., 17(3):167-80.
Zelver, "Measuring antimicrobial effects on biofilm bacteria: from laboratory to field" in *Methods in Enzymology vol. 310 Biofilms.* Doyle (Ed.) Academic Press: San Diego, CA; 1999. Cover page, publisher's page, and pp. 608-628.
Salomon, "Humans have been utilizing natural remedies from plants to treat human diseases for thousands of years" Henrici Society of Microbiology meeting, Minneapolis, MN, Feb. 26, 2014.
Merritt, "Mutation of luxS Affects Biofilm Formation in *Streptococcus mutans*" Apr. 2003 *Infection and Immunity,* 7 1(4): 1972-1979.

\* cited by examiner (A)

(B)

(C)

(A)

(B)

(A)

(B)

(A)

(B)

(A)

(B)

(A)

(B)

SEQUENCE LISTING

```
<160> NUMBER OF SEQ ID NOS: 11

<210> SEQ ID NO 1
<211> LENGTH: 51
<212> TYPE: DNA
<213> ORGANISM: artificial
<220> FEATURE:
<223> OTHER INFORMATION: primer

<400> SEQUENCE: 1
```
ttagcatgct ataaggaggc actcaacatg ggggaggagc gtatgcgaag a              51

<210> SEQ ID NO 2
<211> LENGTH: 33
<212> TYPE: DNA
<213> ORGANISM: artificial
<220> FEATURE:
<223> OTHER INFORMATION: primer

<400> SEQUENCE: 2
taagttacta gttcaagcac gacggcgata acc                                  33

<210> SEQ ID NO 3
<211> LENGTH: 46
<212> TYPE: DNA
<213> ORGANISM: artificial
<220> FEATURE:
<223> OTHER INFORMATION: primer

<400> SEQUENCE: 3
cacatgctaa agaaatcttc tagacagtta cagttacaag aaagtg                    46

<210> SEQ ID NO 4
<211> LENGTH: 26
<212> TYPE: DNA
<213> ORGANISM: artificial
<220> FEATURE:
<223> OTHER INFORMATION: primer

<400> SEQUENCE: 4
ggccatggaa ctgtcaattt cgtgcc                                          26

<210> SEQ ID NO 5
<211> LENGTH: 33
<212> TYPE: DNA
<213> ORGANISM: artificial
<220> FEATURE:
<223> OTHER INFORMATION: primer

<400> SEQUENCE: 5
ttgacagttc catggccggt cactgaacca gga                                  33

<210> SEQ ID NO 6
<211> LENGTH: 33
<212> TYPE: DNA
<213> ORGANISM: artificial
<220> FEATURE:
<223> OTHER INFORMATION: primer

<400> SEQUENCE: 6
taagttacta gttcaagcac gacggcgata acc                                  33

<210> SEQ ID NO 7
<211> LENGTH: 34
<212> TYPE: DNA
<213> ORGANISM: artificial
<220> FEATURE:
<223> OTHER INFORMATION: primer

<400> SEQUENCE: 7
catgcatgcc atggtttcta aggtgaaga attg                                  34

<210> SEQ ID NO 8
<211> LENGTH: 36
<212> TYPE: DNA
<213> ORGANISM: artificial

```
<220> FEATURE:
<223> OTHER INFORMATION: primer

<400> SEQUENCE: 8
ccggcatgct tatttataca attcatccat accatg                              36

<210> SEQ ID NO 9
<211> LENGTH: 15
<212> TYPE: PRT
<213> ORGANISM: artificial
<220> FEATURE:
<223> OTHER INFORMATION: linker

<400> SEQUENCE: 9

Gly Gly Gly Gly Ser Gly Gly Gly Gly Ser Gly Gly Gly Gly Ser
1               5                   10                  15

<210> SEQ ID NO 10
<211> LENGTH: 5
<212> TYPE: PRT
<213> ORGANISM: artificial
<220> FEATURE:
<223> OTHER INFORMATION: Anchor Domain
<220> FEATURE:
<221> NAME/KEY: DOMAIN
<222> LOCATION: (3)..(3)

<400> SEQUENCE: 10

Leu Pro Xaa Thr Gly
1               5

<210> SEQ ID NO 11
<211> LENGTH: 6
<212> TYPE: PRT
<213> ORGANISM: artificial
<220> FEATURE:
<223> OTHER INFORMATION: Anchor Domain
<220> FEATURE:
<221> NAME/KEY: DOMAIN
<222> LOCATION: (5)..(5)

<400> SEQUENCE: 11

Leu Pro Gln Thr Xaa Glu
1               5
```

POLYPEPTDES, CELLS, AND METHODS FOR BIOFILM THERAPY AND DETECTION

CROSS-REFERENCE TO RELATED APPLICATION

This application claims priority to U.S. Provisional Patent Application Ser. No. 62/138,774, filed Mar. 26, 2015, which is incorporated herein by reference.

SEQUENCE LISTING

This application contains a Sequence Listing electronically submitted to the United States Patent and Trademark Office via EFS-Web as an ASCII text file entitled "11004760101_SeqListing_ST25.txt" having a size of 2 KB and created on Mar. 24, 2016.

Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

SUMMARY

This disclosure describes, in one aspect, a fusion polypeptide that includes an anchor domain and a binding domain that specifically binds to a target biofilm. The anchor domain generally includes at least a portion of a cell membrane polypeptide. The binding domain includes a sufficient portion of a polypeptide that specifically binds to a component of a target biofilm to specifically bind to the target biofilm.

In another aspect this disclosure describes a cell that includes the fusion polypeptide summarized above. In some embodiments, the cell can natively possess anti-microbial activity against microbes of the target biofilm. In some embodiments, the cell may be modified to deliver an anti-microbial agent having anti-microbial activity against microbes in the target biofilm. In other embodiments, the cell may be modified to produce a detectable signal. In some embodiments, the cell may be modified so that expression of the fusion polypeptide is induced by a structure or constituent of the target biofilm. In this way, expression of the fusion polypeptide can be induced by the presence of a pathogen of the biofilm.

In another aspect, this disclosure describes a method of inhibiting growth of a target biofilm. Generally, the method includes contacting the target biofilm with an effective amount of a cell modified to specifically bind to the target biofilm, wherein the cell also possesses anti-microbial activity against microbes on the target biofilm. In various embodiments, the cell can destroy, degrade, or weaken the biofilm. In some embodiments, the method can further include contacting the biofilm with supernatant from a cell culture in which the modified cell is grown.

In another aspect, this disclosure describes a method of detecting a target biofilm. Generally, the method includes contacting the target biofilm with an effective amount of a cell modified to specifically bind to the target biofilm, wherein the cell also produces a detectable signal.

In another aspect, this disclosure describes a method of deploying biofilm-degrading materials such as enzymes, biofilm self-destruct signals, quorum sensing molecules, or quenching compounds.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
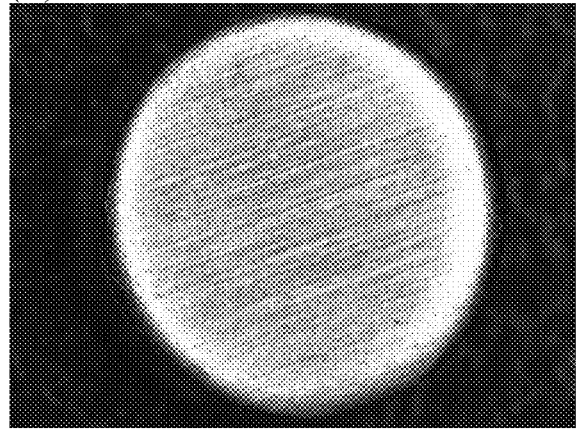
FIG. 1. Images of biofilm growth on steel discs. Panel (A) shows a steel disc with no biofilm growth, negative control. Panel (B) shows a *P. aeruginosa* biofilm grown on steel disc in a 96-well microtiter plate for 48 hours and stained with crystal violet. Panel (C) shows a *P. aeruginosa* biofilm grown on a steel disc in a biofilm reactor for 48 hours and stained with crystal violet. Discs are 5 mm in diameter.
Figure 1:
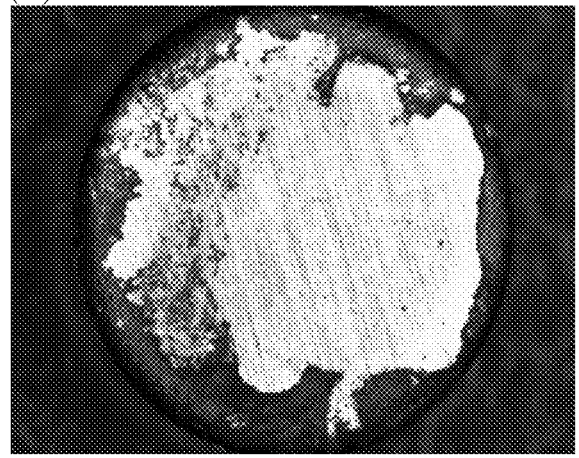
Figure 1:
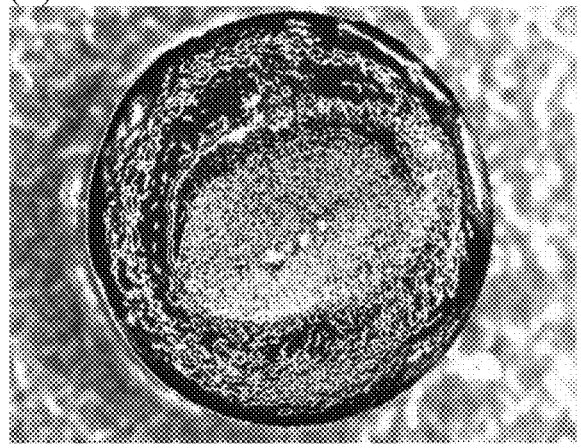

This disclosure describes a model live biotherapeutic product that targets and delivers antimicrobial products to specific biofilms. In one exemplary embodiment, the model live biotherapeutic includes an engineered strain of *Lactococcus lactis* that specifically attaches to *Pseudomonas aeruginosa* biofilm structures using surface display technology.

Biofilms are a morphological state of many pathogenic microbes that can significantly augment their resistance to antimicrobial agents. Biofilms are complex communities of microbial cells that are attached to a surface. The microbial cells encase themselves in a self-organized extracellular polymeric substance (EPS) that is primarily composed of proteins, polysaccharides, and extracellular DNA (eDNA). When these organisms attach to a surface and encase themselves in a biofilm they are more protected from the immune response and external stresses such as antibiotics, chemicals, and physical challenges. In their biofilm state, microbes can be 10 to 1000 times more resistant to antimicrobial treatment than planktonic cells.

Biofilm-associated antibiotic resistance is multifactorial and varies among different organisms. However, many biofilm-producing organisms possess one or more common resistance mechanisms. One common resistance mechanism involves physical protection that the extracellular polymeric substance (EPS) matrix provides for the internal cells. This matrix can slow the diffusion of antibiotics by a factor of 2-3. This slowed diffusion alone is not enough to account for the drastic increase in resistance, but the combination of enzymatic or chemical inactivation of the antibiotic within the matrix and the slowed diffusion may account for the increased resistance. The integrity of the biofilm matrix can be important, as disruption of the matrix can reverse antibiotic resistance of biofilm microbes. Other biofilm-associated resistance mechanisms may include adaptive response to altered environmental conditions (upregulation of stress-response genes), establishment of persister cells, and microenvironment gradients within the biofilm (e.g., low pH, low $pO_2$, high $pCO_2$, and/or low hydration). The enhanced resistance of microbial biofilms may be due to a combination of mechanisms that creates a compounded effect.

One feature of an anti-biofilm strategy is the reproducible growth of the biofilm in vitro. The conditions that are used to grow the biofilm have a significant impact on the architecture of the biofilm and the performance of the antimicrobial therapies. Particularly, the fluid dynamics of the system and the surface on which the biofilm is grown can impact biofilm growth and/or resistance to antimicrobials. In order to create the dynamic flow conditions of the true environment, an apparatus or reactor is typically used to grow the biofilm.

Many biofilm reactors are currently available to grow biofilms under different fluid flow conditions. Biofilm reactors for testing antimicrobial efficacy include batch culture systems and continuous flow systems. Exemplary batch culture systems include the Calgary device, microtiter assay, cover slip culture, the colony biofilm, and biofilm grown on a coupon suspended in a batch culture. Batch culture systems are easy to set up and are amenable to high-throughput testing. Common continuous flow reactor systems include the flow cell, annular reactor, rotating disc reactor, modified Robbins device, drip flow reactor, and biofilm grown in tubing. Continuous flow reactors can achieve a steady state and can provide a more accurate representation of many natural environments.

Standard methods that support biofilm claims are limited. The American society for Testing and Materials (ASTM) released a series of biofilm test methods in 2002-2011 (ASTM E2647-08, ASTM E2562-12, ASTM E2799-12, ASTM E2196-07). Each of the ASTM methods was designed for biofilm growth under different conditions (Table 1). These ASTM methods are useful for standard testing, but generally do not support product efficacy claims with a governmental agency such as the EPA. The EPA released SOPs for biofilm testing in August of 2013 that will support biofilm efficacy claims using the CDC reactor for biofilm growth (EPA MB-19-02, EPA MB-20-01).

TABLE 1

| ASTM Standard methods for biofilm growth | | | |
|---|---|---|---|
| Method | Reactor used | Year published | Growth conditions |
| ASTM E2196-07 | Rotating Disk Reactor | 2002 | Submerged, Continuous flow, Medium-shear |
| ASTM E2562-12 | CDC Reactor | 2007 | Submerged, Continuous flow, High-shear |
| ASTM E2647-08 | Drip Flow Reactor | 2008 | Air/liquid interface, Continuous flow, Laminar flow/low-shear |
| ASTM E2196-07 | MBEC | 2011 | Batch culture, low to medium-shear |

Biofilm growth under laminar flow conditions at the air/water interface is a way to create biofilm growth conditions that represent the environment in which biofilms naturally grow. The drip flow biofilm reactor described in ASTM E2647-08 is one exemplary biofilm reactor that fits these criteria. This drip flow reactor has been recommended to model multiple disease states such as, for example, chronic wound infections, lung infections, and urological infections. However, the current drip flow reactor is only capable of low throughput testing (4 coupons per growth cycle), and the biofilm growth on each coupon is not uniform.

Many of the current treatment options for biofilm infections are ineffective. This disclosure describes a novel strategy that uses a probiotic microorganism to target and deliver antimicrobial products to pathogenic biofilms. One exemplary embodiment involves the design of a model lactic acid bacterial (LAB) strain that specifically binds to a target biofilm such as, for example, a *P. aeruginosa* biofilm, and then engineering the model probiotic strain (e.g., a lactic acid bacterium strain) to produce an anti-biofilm therapeutic only in the presence of the target biofilm.

Bacterial surface display was used to design the model probiotic bacterium to attach to an exemplary *Pseudomonas* biofilm. Surface display involves the fusion of a protein of interest to a cell membrane protein that is native to bacterial cells. This enables the protein of interest to be displayed on the cell membrane. In some embodiments, the protein of interest can be an antibody single-chain variable fragment (scFv) that binds specifically to *P. aeruginosa* alginate (Pier et al., 2004, *J Immunol* 173(9), 5671-5678). One exemplary cell membrane protein is a sortase-dependent cell membrane protein of *Lactobacillus plantarum*. Coding regions for these proteins were fused and added to an *E. coli*/LAB shuttle vector, regulated under a nisin-inducible promoter. The shuttle vector was introduced into the model lactic acid bacterium strain.

The model probiotic strain can be engineered to produce an anti-biofilm therapeutic in the presence of a target biofilm. The therapeutic product can disrupt and/or inhibit the target biofilm. Expression of the therapeutic product can be under the regulation of a promoter that is derived from the microbe of the target biofilm so that the anti-biofilm therapeutic is only produced in the presence of the target biofilm. The therapeutic can be, for example, a biofilm-disrupting enzyme such as a DNase or an alginate lyase, and/or it could be an antimicrobial peptide that kills cells of the target biofilm. Preliminary testing was performed using a model system that employed engineered *Lactobacillus plantarum* cells as the model probiotic bacterium against a clinical strain of *P. aeruginosa* as the model target biofilm.

Figure 2:
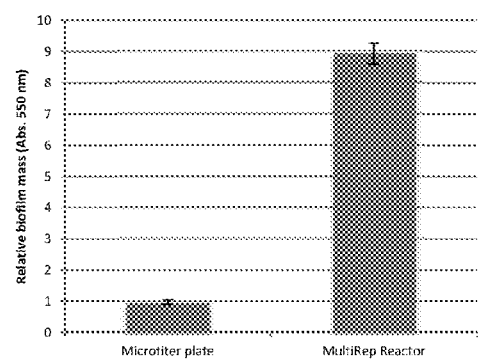
FIG. 2. Quantitative comparison of *P. aeruginosa* grown on steel discs in a microtiter plate or a biofilm reactor for 24 h using the crystal violet assay.

Growing a uniform biofilm over the surface of coupons maximizes the amount of biofilm on the coupon and minimizes variation between coupons. FIG. 1 shows images of *P. aeruginosa* biofilm grown on stainless steel discs. Biofilms were grown on the discs in either a microtiter plate or in a biofilm reactor, then stained with crystal violet. A uniform biofilm over the surface of the coupon could be achieved using the biofilm reactor (FIG. 1, panel C). The biofilm produced on the steel discs in the 96-well plate grew only around the periphery of the coupon (FIG. 1, panel B). FIG. 2 shows a quantitative comparison of the amount of biofilm produced when grown in the biofilm reactor compared to a microtiter plate.

This disclosure describes a model biotherapeutic agent that targets microbial biofilms. Generally, the biotherapeutic agent includes a fusion polypeptide that includes an anchor domain and a binding domain. Generally, the anchor domain includes at least a portion of a cell membrane polypeptide so that the fusion polypeptide can be anchored into the cell membrane of a host cell such as, for example, a probiotic microbe. Generally, the binding domain includes a sufficient portion of a polypeptide that specifically binds to a component of a target biofilm so to provide specific binding to the target biofilm.

Figure 3:
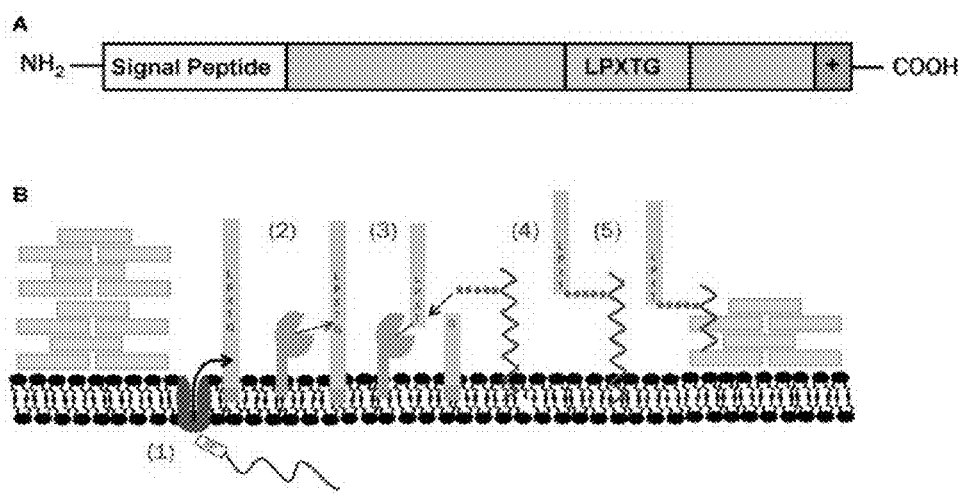
FIG. 3. Illustration of the sortase-dependent anchoring in Gram-positive bacteria. Panel (A) shows a schematic diagram of a fusion polypeptide with two domains that facilitate sortase anchoring, the anchor domain (e.g., signal peptide) and the binding domain (e.g., LPXTG (SEQ ID NO:10) motif). Panel (B): In the illustrated embodiment, the signal peptide is involved in localizing the fusion polypeptide to the membrane. The Sec system recognizes the signal peptide and exports the protein to the exterior (1). The sortase then recognizes the substrate (LPXTG (SEQ ID NO:10)) (2), cleaves between glycine and threonine (3), threonine then forms a bond with the pentapeptide crossbridge (4). Finally, the sortase substrate becomes part of the normal cell-wall construction.

In an exemplary embodiment, a native cell-membrane protein found in *L. plantarum* was used to display and anchor the alginate-binding scFv protein on the cell membrane of the engineered model lactic acid bacteria (LAB) strain. Surface proteins mediate interactions between a bacterium and its environment. In lactic acid bacteria, the sortase enzyme is involved in covalently attaching a subgroup of proteins called sortase-dependent proteins (SDPs) to the cell membrane. This is a two-part process that involves both protein targeting to the membrane and covalent anchoring of the protein to the cell membrane. The targeting of the protein usually involves the secretory (Sec) pathway or the twin-arginine translocation (TAT) pathway. The Sec pathway appears to be much more common in lactic acid bacteria. In the Sec pathway, unfolded proteins that contain an N-terminal leader peptide, a hydrophobic core, and a specific C-terminal sequence that is recognized by the Sec machinery are targeted to the cell exterior. One group of SDPs that are covalently attached to the cell membrane of lactic acid bacteria is the LPXTG (SEQ ID NO:10)-anchored proteins. These proteins contain a specific C-terminal motif (LPXTG (SEQ ID NO:10)), a positively charged tail, and a C-terminal hydrophobic region that is recognized by the sortase enzyme (FIG. 3, panel A). However, in many Lactobacilli the C-terminal motif is LPQTXE (SEQ ID NO:11), which also is functional in *Lactococcus* spp.

The exemplary cell-membrane protein used in this construct is an LPQTXE (SEQ ID NO:11)-anchored SDP identified as lp 2578. Previously, this protein was used to display an oncofetal antigen (OFA) on the surface of *L. plantarum* for a mucosal cancer vaccine (Fredriksen et al., 2010). To display the OFA on the cell membrane, the OFA gene was fused to the anchor sequence on the N-terminal side of both the hydrophobic region and the LPQTXE (SEQ ID NO:11) motif, but on the C-terminal side of the signal peptide. Surface expression of this protein is highest using a truncated medium-length anchor.

In an exemplary embodiment of the fusion polypeptides described herein, the binding component specifically binds to a unique component of the target biofilm that is not commonly found in other biofilm structures, thus enabling specific binding of the engineered lactic acid bacterium to the target biofilm even in the presence of other natural biofilms. As used herein, "specific" and variations thereof refer to having a differential or a non-general affinity, to any degree, for a particular target. Mucoid strains of *P. aeruginosa* contain a unique EPS component called alginate. Alginate is a high-molecular weight polysaccharide having non-repeating D-mannuronic acid and L-guluronic acid residues. It is only found in some brown algae species, and *Azotobacter* and *Pseudomonas* bacteria. The algal alginate is, however, different from the bacterial form in that the bacterial version is O-acetylated.

In an exemplary embodiment, the binding component includes a short chain fragment variable (scFv) fragment derived from human monoclonal antibodies (mAbs) that bind to *Pseudomonas* alginate (Pier et al., 2004, *J Immunol* 173(9), 5671-5678). These mAbs mediate immunological killing of *Pseudomonas* mucoid strains as well as non-mucoid, low alginate producing strains. In particular, mAb (F429) has broad overall alginate binding activity over a wide range of *Pseudomonas* isolates from cystic fibrosis patients. The scFv region of the F429 mAb (Pier et al., 2004, *J Immunol* 173(9), 5671-5678) was used, joining the $V_H$ and $V_L$ chains of the scFv with a linker peptide (GGGGS)$_3$ (SEQ ID NO:9) that enables proper linkage and flexibility between the light and heavy chains of the scFv. In order to display this alginate binding protein on the cell membrane, the synthesized F429 scFv DNA sequence was fused to the N-terminal side of the SDP anchor peptide DNA sequence and to the C-terminal side of the signal peptide DNA sequence. This construct was then cloned into an *E. coli*/LAB shuttle vector and is regulated by a nisin-inducible promoter.

While described herein in the context of an exemplary embodiment in which the host cell is the lactic acid bacterium *Lactobacillus plantarum*, the fusion polypeptides and methods described herein can involve host cells from any species found naturally in the human gastrointestinal system and/or considered to be probiotic. Exemplary alternative species of host cells include, for example, a *Lactobacillus* spp., a *Lactococcus* spp., a *Bacillus* spp., a *Streptococcus* spp., a *Bifidobacteria* spp., a *Bacteroides* spp., or a *Clostridium* spp.

Similarly, while described herein in the context of an exemplary embodiment in which the native source of the anchor domain of the fusion polypeptide is the lactic acid bacterium *Lactobacillus plantarum*, the fusion polypeptides and methods described herein can involve a cell membrane polypeptide natively expressed by any species of microbe so long as the anchor domain is expressable in the host cell. Thus, the native source of the cell membrane polypeptide need not be the host cell.

Also, while described herein in the context of an exemplary embodiment in which the target biofilm includes *Pseudomonas aeruginosa*, the fusion polypeptides and methods described herein can involve a target biofilm that includes any medically-relevant biofilm including species involved in an oral/dental system, the urogenital tract, wound infection, implants, prosthetics, the gastrointestinal tract, pulmonary infections and/or a microbial species implicated in cancer. In certain embodiments, the target biofilm can include an industrially-relevant biofilm.

Finally, while described herein in the context of an exemplary embodiment in which the binding component in an antibody fragment, the fusion polypeptide and/or methods described herein can involve any polypeptide or polypeptide fragment that is capable of providing the specific binding function of the binding domain—i.e., capable of specifically binding to the target biofilm. As used herein, specifically binding to the "target biofilm" includes binding to a component of the biofilm matrix and/or binding to a membrane component of the biofilm microbe.

A microbe that can attach to a biofilm can inhibit growth and/or eliminate the biofilm through deployment of extracellular products. Exemplary strategies for treating biofilm-associated infection can involve substances able to destroy or weaken the biofilm matrix, substances that destroy persister cells, quorum-quenching enzymes, substances that cause biofilm self-destruction, and strategies to boost antimicrobial action. The system described herein can employ any one or any combination of these strategies. It is also possible that the probiotic strain could natively have the capability of inhibiting or destroying the biofilm. For example, a *L. plantarum* supernatant was shown to inhibit *P. aeruginosa* through a quorum quenching mechanism. Additionally, lactic acid bacteria strains can modulate the immune system and can inhibit and/or prevent infections by pathogenic microbes. Attachment of probiotic organisms to the biofilm structures may enhance immune system activity against infection. Some lactic acid bacteria are also known to enhance wound healing. To enhance the native ability of the probiotic to eradicate biofilms, heterologous expression of anti-biofilm components can be implemented. For example, alginate lyase and/or DNase can enhance antibiotic killing of *P. aeruginosa* biofilm cells. Additionally, heterologous expression of a protein antibiotic may be used. For example, pyocin S2 is a high molecular weight protein antibiotic that not only kills pathogenic cells, but also destroys the biofilm matrix. Additional compounds or proteins could be expressed to enhance wound healing and/or immunomodulatory activities.

Bacterial surface display was used to express F429 scFv on the cell membrane of model probiotic *L. lactis*. The F429 scFv specifically binds to the model *P. aeruginosa* target biofilm. The F429 scFv was fused to a native LAB sortase-dependent cell membrane protein to enable the attachment of the probiotic host cell *L. lactis* to the biofilm structure of *P. aeruginosa*. Alginate, a component of the *P. aeruginosa* EPS, was chosen as the target for binding because it is a unique polysaccharide component not commonly found in other microbial biofilms. *P. aeruginosa* was chosen as a target for binding because it is a model organism for biofilm testing and is a known antibiotic-resistant human pathogen.

Figure 4:
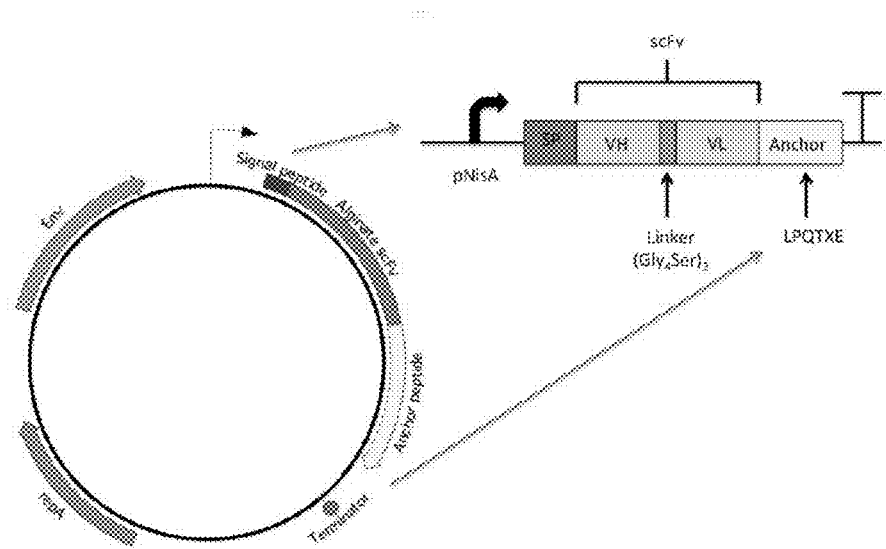
FIG. 4. An exemplary binding cassette construct. pNisA, nisin inducible promoter within the pMSP3545 vector. SP, signal peptide sequence. VH, heavy chain variable region sequence. VL, light chain variable region sequence. Anchor, sortase-dependent cell membrane protein containing a hydrophobic region N terminally to the LPQTXE (SEQ ID NO:11) motif.

The genetic construct for the binding cassette (scFv F429 DNA sequence fused between the signal peptide and the anchor peptide of 1p 2578 sequences) was successfully made and verified by sequencing (FIG. 4).

The binding cassette was constructed as described in Example 2. This construct was then cloned into the pMSP3545 vector after the nisin-inducible pNisA promoter, and sequenced to verify proper gene orientation and sequence integrity. Any additional cloning was carried out in the nisin-inducible pMSP3545 vector to avoid any toxicity issues in *E. coli*.

Figure 5:
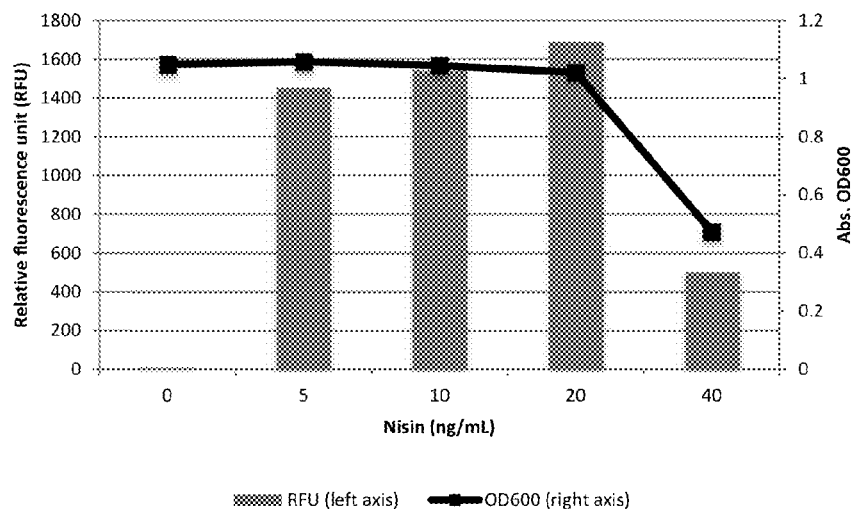
FIG. 5. Effect of nisin concentration on GFP expression and cell density for *L. lactis* (pJE7).

GFPsp was added to the vector as a reporter protein. The expression of GFPsp was placed under the regulation of the same promoter as the binding cassette. The nisin concentration necessary for expression of these proteins in *L. lactis* was evaluated using a range of nisin concentrations (0-40 ng/mL; FIG. 5). The GFP expression from each of these cultures was measured using a fluorescent plate reader, and compared to the cell density after six hours of incubation after the time of induction. GFP expression was greatest at a nisin induction concentration between 5 ng/ml and 20 ng/mL, and a higher nisin concentration (40 ng/mL) inhibited growth of the cultures. 10 ng/mL was chosen as the induction concentration going forward.

Figure 6:
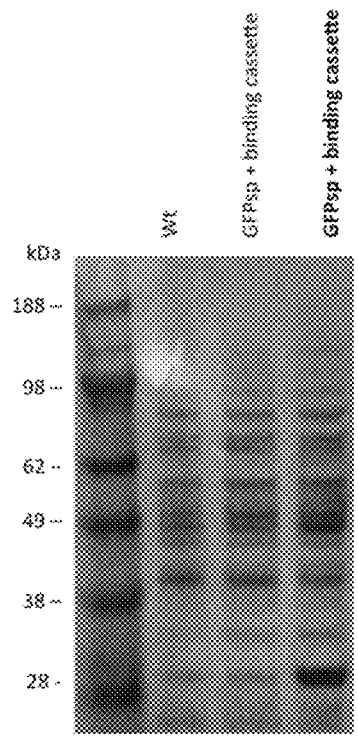
FIG. 6. LDS-PAGE separation of membrane fractions. Panel (A) shows cytoplasmic fractions of cellular components (pellet from 10000×g centrifuge step). Panel (B) shows cell membrane fractions (pellet from 100000×g centrifuge step). Uninduced cultures are in regular font. Induced cultures are shown in bold font. Expected size of GFP—28 kDa; Expected size of binding cassette protein—47.23 kDa.
Figure 6:
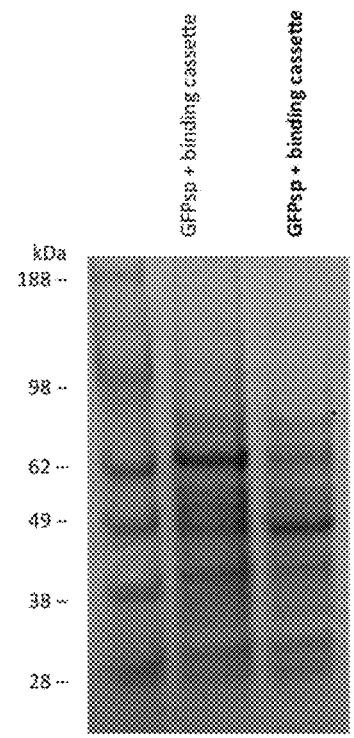

The scFv F429 was successfully fused to the SDP 1p 2578 and displayed on the cell membrane of *L. lactis*. Cytoplasmic and cell membrane fractions of both uninduced (regular font) and induced (bold font) *L. lactis* cultures containing both GFPsp and the binding cassette were separated and prepared. The proteins from these cell fractions were then compared via lithium dodecyl sulfate (LDS) polyacrylamide gel electrophoresis (FIG. 6). GFP (expected size: 28 kDa) was found only in the cytoplasmic fraction (FIG. 6, panel A) since there is no signal peptide attached to the GFP for secretion outside the cell. The binding cassette protein (expected size: 47.23 kDa) was found primarily in the cell membrane fraction (FIG. 6, panel B). The binding cassette proteins were not found in the culture supernatant (data not shown), indicating that the scFv F429 fused to the 1p 2578 SDP was anchored to the peptidoglycan of the cell wall of the *L. lactis* cells. The more intense band seen around 62 kDa in the uninduced cell membrane faction (FIG. 6, panel A) may be due to a difference in total protein concentration between the uninduced and induced cultures.

Figure 7:
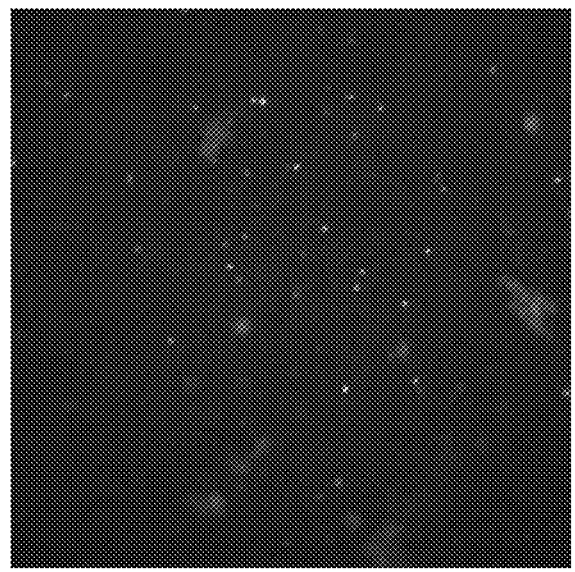
FIG. 7. Characterization of attachment to *P. aeruginosa* NH57388A biofilms on steel discs. Biofilms were grown on steel discs in a biofilm reactor. *L. lactis* (pJEGFPsp—GFP only; panel (A)) and *L. lactis* (pJE7—GFP+binding cassette; panel (B)) were exposed to the biofilms and washed prior to imaging. Images were taken with a fluorescent microscope at 100× magnification.
Figure 7:
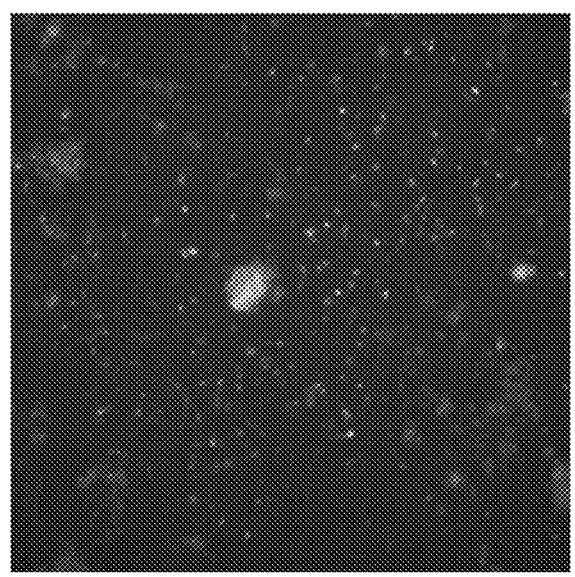

Next, to determine if the engineered cells would specifically bind to *P. aeruginosa* alginate-containing biofilms, the *L. lactis* cells expressing GFPsp alone or GPFsp and the binding cassette were exposed to *P. aeruginosa* NH57388A cultivated as biofilms on steel discs, washed five times, and viewed with an epifluorescence microscope using an FITC filter (FIG. 7). Samples were prepared in duplicate, and the images were taken of areas that represented the majority of the sample surface. The images show that a higher number of cells expressing the binding cassette (FIG. 7, panel B) were recovered than the number of cells that did not have the ability to make the binding cassette protein (FIG. 7, panel A). This indicates that the binding cassette protein was not only expressed on the cell membrane of *L. lactis*, but also enhanced binding to *P. aeruginosa* alginate-producing biofilms. Alginate production by *P. aeruginosa* was verified using a carbazole assay, which confirmed that *P. aeruginosa* NH57388A biofilms grown in a 96-well plate produced approximately 12 μg/well of alginate.

Figure 8:
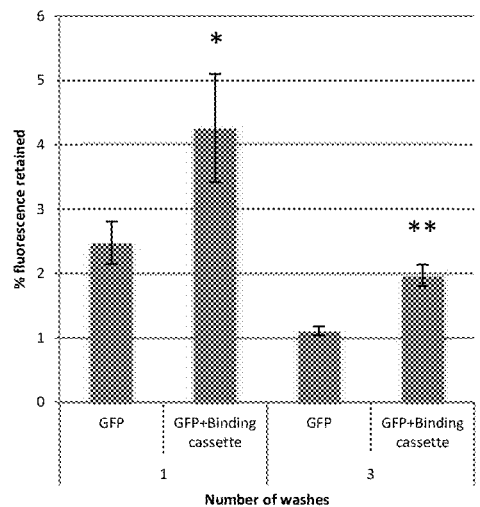
FIG. 8. Quantitative binding assay—biofilm grown in 96-well plate. Panel (A) shows data for the alginate producing strain *P. aeruginosa* NH57388A; Panel (B) shows data for the alginate knockout strain *P. aeruginosa* (PAO1 ΔAlgD). The strains were grown on the well surfaces of a 96-well plate and exposed to *L. lactis* strains (pJEGFPsp—GFPsp only) or (pJE7—GFPsp+binding cassette). The cells were washed a number of times and the percentage of fluorescence retained was calculated. (*) Indicates statistical significance between GFP only and GFP+binding cassette for one wash (p<0.05). (**) Indicates statistical significance between GFP only and GFP+binding cassette for three washes (p<0.01). Error bars are based on n=8.
Figure 8:
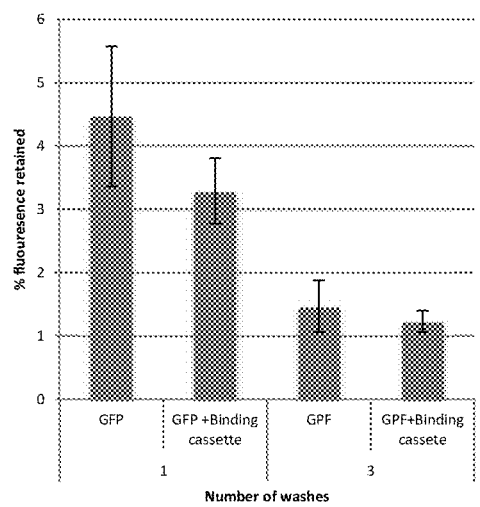

The fluorescent microscope images qualitatively indicate that the engineered strain of *L. lactis* exhibits enhanced binding to biofilm structures containing alginate. Next, a quantitative study to analyze the binding of the engineered *L. lactis* strain to the biofilms was designed. Biofilms of both the alginate producing strain (PA NH57388A) and a non-alginate producing strain (PAO1 ΔalgD) were grown on the well surfaces of a 96-well plate. *L. lactis* cells expressing GFP only, or GFP and the binding cassette were then exposed to the biofilms for 3.5 hours, washed, and the percentage of fluorescence retained was determined by dividing by the starting fluorescence of each culture. This calculation was performed because the starting fluorescence of the GFP only and the GFP-binding cassette strains had different initial fluorescence expression. The percentage of fluorescence retained after exposure to the alginate-containing biofilms is shown in FIG. 8, panel A, while the results after exposure to the non-alginate producing strain are shown in FIG. 8, panel B. The results indicate that there was a significant difference in binding observed between the *L. lactis* strain that contained the binding cassette and the strain that expressed GFP alone. A student's t-test was performed to compare the statistical significance of the means obtained for each comparison. As the number of washes increases in FIG. 8, panel A, the statistical significance increases between the percent fluorescence retained for the strain that has the binding cassette and the GFP-only strain. Additionally, when the GFP-only and GFP-binding cassette strains of *L. lactis* are exposed to biofilms that do not contain alginate, the difference between the two strains is lowered as the number of washes increases (FIG. 8, panel B). Therefore, expression of the binding cassette in *L. lactis* enabled specific binding to *P. aeruginosa* biofilms that contain alginate.

Figure 9:
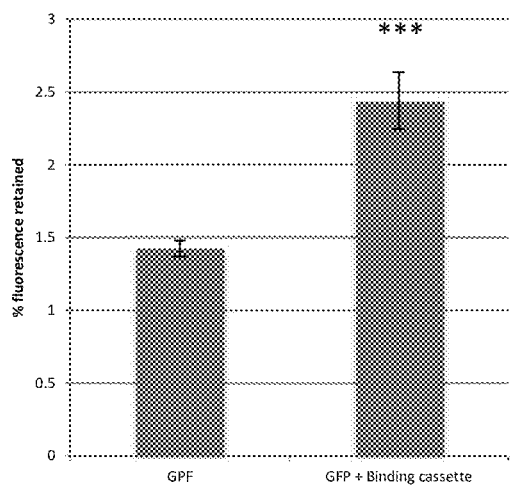
FIG. 9. Quantitative binding assay—biofilm grown in a biofilm reactor. *P. aeruginosa* NH57388A was grown on steel discs in the biofilm reactor and exposed to *L. lactis* (pJEGFPsp—GFP only) or *L. lactis* (pJE7—GFP+binding cassette). Panel (A) shows the percentage of fluorescence retained by the *L. lactis* cells. Panel (B) shows CFU of *L. lactis*/disc recovered. (*) Indicates statistical significance between GFP only and GFP+binding cassette (p<0.05). (***) Indicates statistical significance between GFP only and GFP+binding cassette for 3 washes (p<0.001). Error bars are based on n=6 for panel (A), and n=4 for panel (B).
Figure 9:
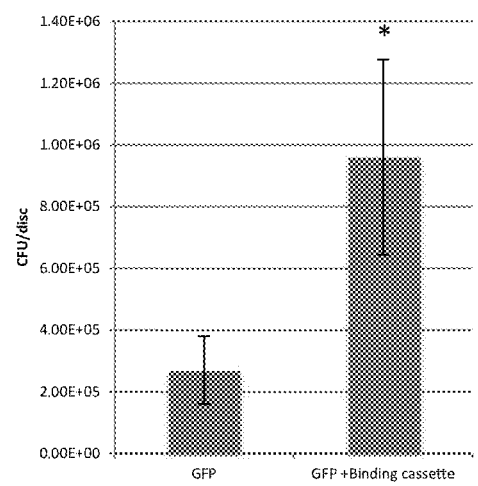

An additional quantitative study was performed with the *P. aeruginosa* biofilms grown on steel discs in the biofilm reactor. For this study, both the percent fluorescence retained and the CFU/disc recovered was determined for each group studied (FIG. 9). The results from this study again indicated that there was a statistically significant difference between the GFP-only and GFP-binding cassette cells recovered. For the CFU/disc determination, the *L. lactis* cells recovered were diluted and plated onto MRS agar. Normally, *L. lactis* is grown on M17+glucose media, but MRS was chosen because *P. aeruginosa* does not grow on this media. The *L. lactis* did not grow as quickly on the MRS media, and the colonies were smaller.

Figure 10:
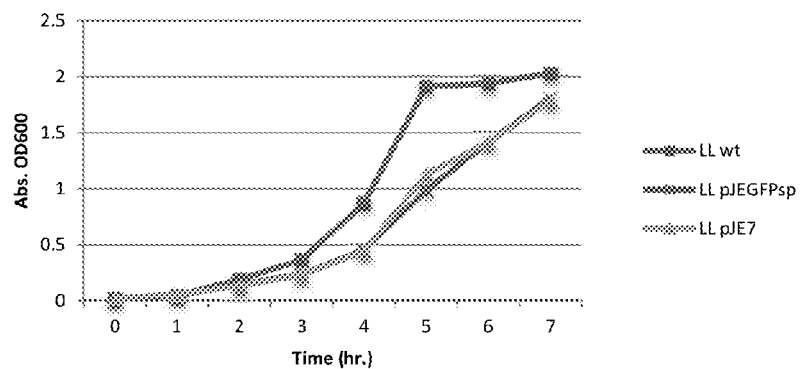
FIG. 10. Growth rate of *L. lactis* strains over time. LL=*L. lactis*, pJEGFPsp (GFP expression only), pJE7 (GFP+binding cassette). Each strain was induced with nisin (10 ng/mL) at the two-hour time point.

Next, a study was performed to determine the effect that expression of these proteins may have on *L. lactis* growth over time. Three strains of *L. lactis* were compared: *L. lactis* Wt, *L. lactis* pJEGFPsp (GFP), and *L. lactis* pJE7 (GFP-binding cassette) over a total time of seven hours. After two hours of growth, protein expression was induced with nisin (10 ng/mL). The expression of these recombinant proteins in *L. lactis* does appear to have a slight effect on growth rate initially (FIG. 10). However, there does not appear to be a significant difference between the growth rate of the GFP-only and the GFP-binding cassette strain.

The biofilm attachment studies just described were done in *L. lactis* due to the ease of genetic manipulation, and because the nisin-inducible system is well characterized in this organism. However, the development of anti-biofilm activity can involve the implementation of the binding components into a different lactic acid bacterium strain with useful enzymatic, inhibitory, wound healing, or immune-modulation activities. Exemplary lactic acid bacteria strains include, for example, an *L. plantarum* spp. Native *L. plantarum* strains can have anti-biofilm properties.

Figure 14:
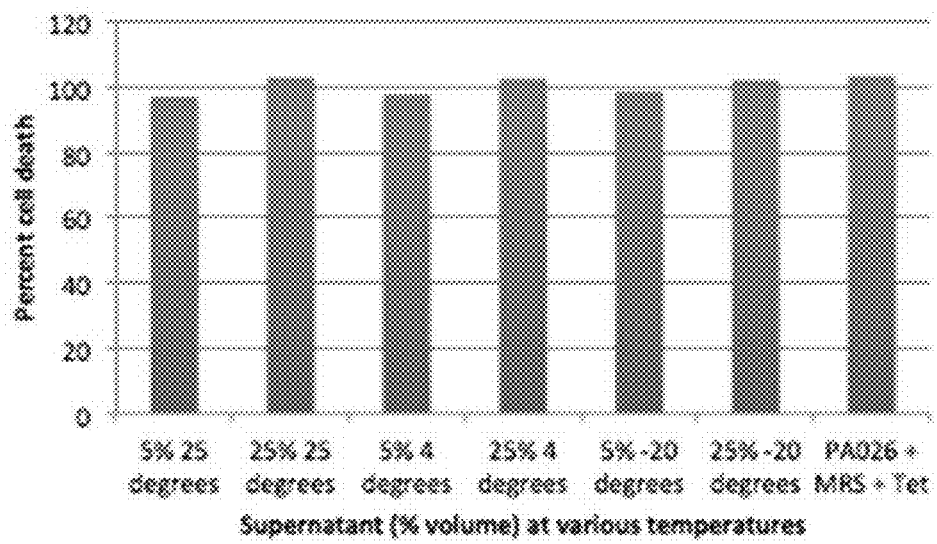
FIG. 14. Percent cell death of *P. aeruginosa* following treatment with WCFS1 supernatant that was stored at various temperatures for four hours.

In order to test the relative stability of the antimicrobial properties of *L. plantarum* supernatants during storage conditions, samples were incubated at various temperatures and tested for activity. Supernatants from an overnight culture of *L. plantarum* WCFS1 were stored at −20° C., 4° C., or 25° C. for four hours. They were then tested against planktonic *P. aeruginosa* to determine their ability to inhibit growth after incubating at various temperatures. At all temperatures, wells with either 5% WCFS1 supernatant or 25% WCFS1 supernatant (by volume) resulted in nearly 100% cell death (FIG. 14). These results suggest that the antimicrobial activity is stable at low temperature and at high temperature (−20° C. to 25° C.) over short time spans (up to about four hours).

Figure 15:
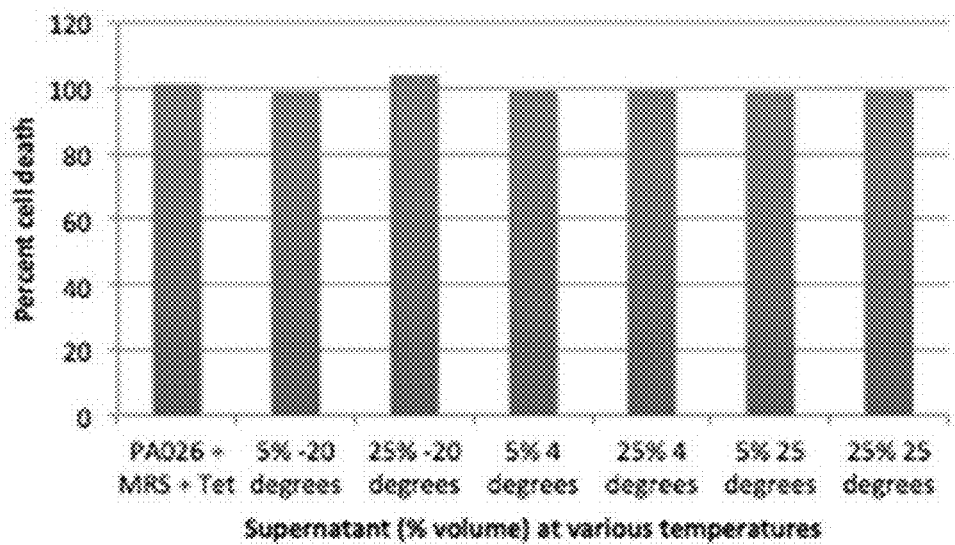
FIG. 15. Percent cell death of *P. aeruginosa* following treatment with WCFS1 supernatant that was stored at various temperatures for 24 hours.

In order to determine the stability of the activity over longer periods of time, the experiment was repeated. Supernatant was removed from an overnight culture of WCFS1 and stored at −20° C., 4° C., or 25° C. for approximately 24 hours. It was tested against planktonic *P. aeruginosa* using a broth dilution assay to determine percent cell death. Supernatant stored at all temperatures gave nearly 100% cell death at both 5% and 25% (v/v) (FIG. 15). Collectively, the results shown in FIG. 14 and FIG. 15 suggest that the antimicrobial components of at least one *L. plantarum* isolate are stable as a complex supernatant at a variety of temperatures over the time span of 24 hours.

Figure 11:
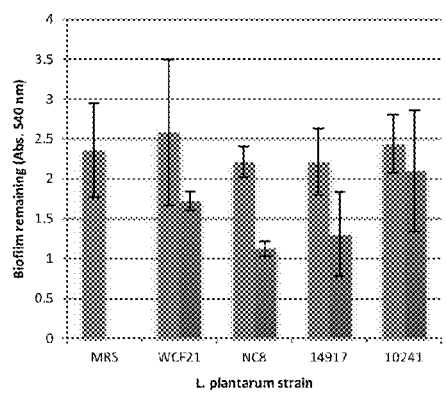
FIG. 11. *L. plantarum* supernatant effect on *P. aeruginosa* PAO26 biofilms. Biofilms were grown for 24 h, then treated with raw, or neutralized supernatants from *L. plantarum* cultures for an additional 24 h. Following treatment, the crystal violet assay was performed to quantify the biofilm remaining. Panel (A) is 5% supernatant; Panel (B) is 25% supernatant concentration in the final test volume. MRS (pH 6.5) is the broth that the *L. plantarum* strains were grown in. Error bars are based on n=3.
Figure 11:
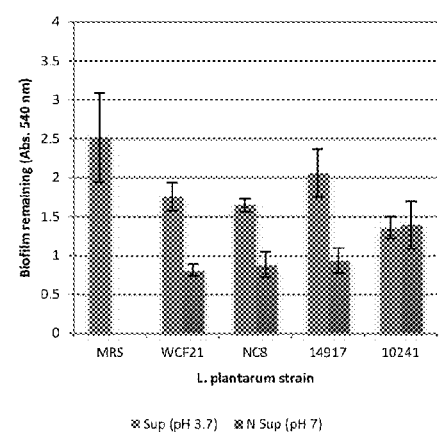
Figure 12:
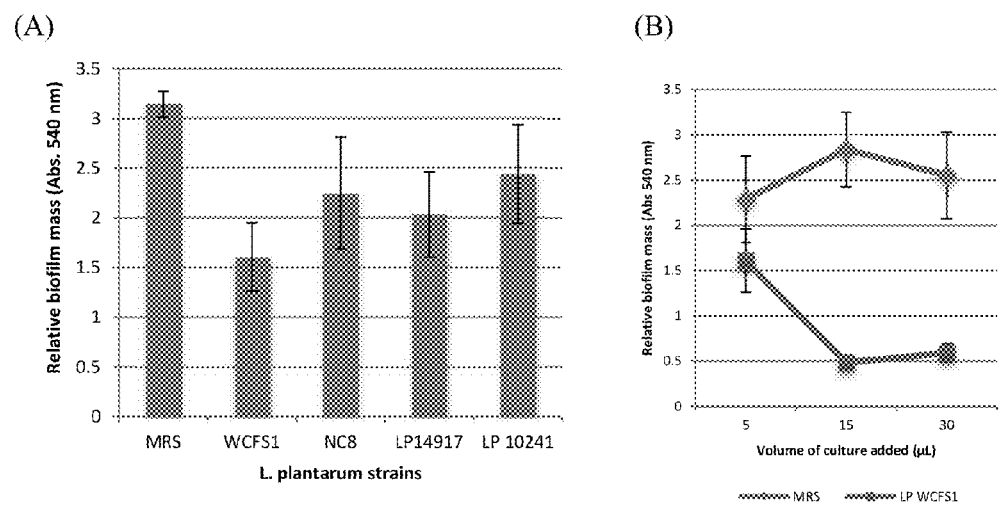
FIG. 12. Removal of *P. aeruginosa* PAO26 biofilms with *L. plantarum* cell cultures. In panel (A), biofilms were grown for 24 hours, and treated with 2 µL of *L. plantarum* cell culture for an additional 24 hours (Error bars based on n=3). Panel (B) shows additional testing of biofilm removal with *L. plantarum* WCFS1 using different starting volumes of *L. plantarum* culture, final volume in each well was 160 µL (Error bars based on n=4).

Preliminary testing with a number of wild-type *L. plantarum* strains was performed to determine which strain, if any, exhibits natural inhibitory activity on *P. aeruginosa* biofilms. In this study, both the supernatants (FIG. 11) and the cell cultures (FIG. 12) of four *L. plantarum* strains (WCFS1, NC8, 14917, and 10241) were tested against *P. aeruginosa* biofilms. Overnight cultures of each of the *L. plantarum* strains were prepared, and either the supernatants (untreated or pH neutralized), or the cell cultures were added to pre-formed *P. aeruginosa* PAO26 biofilms and the amount of biofilm removed was analyzed using the crystal violet assay. The pH studies were done to determine the potential role of pH in biofilm removal and antimicrobial activity. In each of these studies in this section, *P. aeruginosa* PAO26 (a mucoid isolate from the lungs of a cystic fibrosis patient) was used instead of *P. aeruginosa* NH57388A because this strain formed robust biofilms more quickly than the NH57388A strain.

The results from these studies indicate that some of the *L. plantarum* cells may have the ability to degrade or remove *P. aeruginosa* biofilm structures. The neutralized supernatants, for some of the strains, appeared to have a greater ability to remove *P. aeruginosa* biofilm than the acidic (natural) supernatants. This indicates that the low pH was not the primary mechanism of biofilm removal, and there may be products made by these organisms that have a *P. aeruginosa* biofilm removal effect that is enhanced under neutral pH conditions. The results from the *L. plantarum* cell culture study (FIG. 12) indicate that some of the *L. plantarum* cells, when grown in the presence of *P. aeruginosa* biofilms, may also have a biofilm removal effect.

Figure 13:
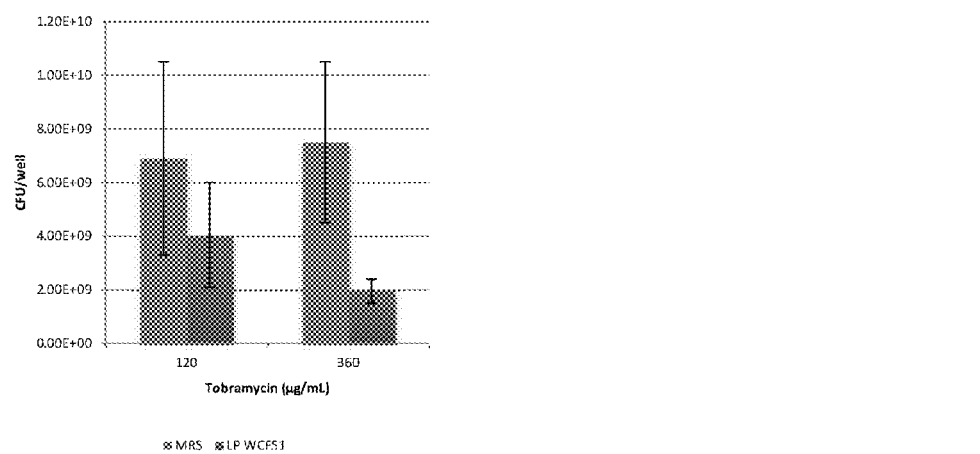
FIG. 13. Tobramycin and *L. plantarum* cell cultures against *P. aeruginosa* PAO26 biofilms. The data shows the effect that tobramycin, in combination with *L. plantarum*, has on *P. aeruginosa* biofilm cell viability.

Based on the results of the study comparing the biofilm removal activity of multiple *L. plantarum* strains, strain WCFS1 was chosen for further testing. One application of an engineered lactic acid bacterium strain may be to enhance the efficacy of antibiotic treatments against biofilms. *L. plantarum* WCFS1 cell cultures were evaluated for the ability to enhance the antimicrobial activity of tobramycin against *P. aeruginosa* biofilms. Tobramycin is a commonly used antibiotic for *P. aeruginosa* infections, but along with many of the treatment options for this pathogen, is much less effective against the biofilm-associated cells. For this study, *P. aeruginosa* PAO26 was grown on the well surfaces of a 96-well plate. The biofilms were then treated with *L. plantarum* WCF S1 cell cultures overnight, followed by treatment with tobramycin (120 µg/mL or 360 µg/mL). FIG. 13 indicates that the pre-treatment of *P. aeruginosa* biofilms with *L. plantarum* cell cultures may increase the activity of tobramycin against *P. aeruginosa* biofilms.

While described above in the context of an exemplary embodiment in which the antibiotic treatment includes treatment with tobramycin, the methods described herein can involve alternative antimicrobial treatments such as, for example, an antibiotic, an antifungal, an antimicrobial peptide (including, e.g., anti-microbial enzymes), an enzyme that degrades the biofilm matrix, and/or any quorum quenching or quorum sensing molecule.

Due to the combination of antibiotic resistance and a dearth of new antibiotics entering the pipeline, there is a global need for a new paradigm in infection prevention strategies. Biofilms have been highlighted as one of the major contributing factors for chronic bacterial infections that, in some cases, can be essentially untreatable. A model strain of a probiotic host cell (*L. lactis*) was designed to display a heterologous alginate-binding scFv on its cell wall by anchoring it to a native lactic acid bacterium sortase-dependent cell membrane protein. The expression of these proteins was not only directed and anchored to the cell membrane of the *L. lactis* cells, but they also increased the ability of this organism to attach to a model biofilm (a *P. aeruginosa* biofilm). The fusion protein platform described herein can be a generalized strategy for developing microbial therapeutics that deliver drugs to the precise location of pathogenic biofilms.

Biofilm degrading enzymes such as alginate lyase, DNase, or dispersin B can be heterologously expressed and deployed by an engineered probiotic strain once it has attached to the biofilm structures. Expression of antimicrobial peptides could also be employed to aid in killing of the pathogenic cells once the biofilm has been degraded. Yet another strategy could be to deliver quorum quenching enzymes and/or signaling peptides that reduce antibiotic-resistance transfer among cells in a particular biofilm.

The ability to direct the attachment of a probiotic organism to biofilm structures has a wide range of applications. The model system described herein may be adapted to employ alternative probiotic microbes and/or target alternative biofilms. Our exemplary model system uses the binding protein scFv F429 to target *P. aeruginosa* biofilm structures. This binding protein can easily be substituted, however, with an alternative binding protein that specifically targets biofilm structures produced by alternative microbes. Thus, the system described herein can be used to target any other organism that forms a biofilm, and has a unique component for attachment. Second, the ability to direct the attachment of a probiotic organism to alginate could be useful in biocatalysis. Polymer matrices that include, for example, agar, polyacrylamide, chitin, and/or alginate are commonly used as whole-cell entrapment/immobilization agents in biocatalysis. The agents can be limited, however, due to limitations in the transport of substrates through the matrix. If the cells can be immobilized on a monolayer of, for example, alginate, one can increase because the immobilized cells would have more direct contact with the biocatalysis substrates. Third, this system could be used to enhance biofilm growth for application in bioremediation of toxic chemicals from wastewater. And finally, this system could be used for biofilm diagnostic purposes. Biophotonic imaging is used to study bioluminescent bacteria in vivo, and allows one to continually monitor biofilm infections in animals without disrupting the biofilm over the course of the disease. The system can be used in this fashion to diagnose biofilm infections in humans. The fluorescent probiotic cells that bind to specific biofilms could be deployed to identify the pathogen and the location of the biofilms in the host.

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Strains and Growth Conditions

For routine growth, Pseudomonas aeruginosa ATCC 15442 was taken from a frozen glycerol stock (−80° C.) and plated on trypticase soy agar (TSA). Single colonies were used to inoculate trypticase soy broth (TSB) (30 g/L), and cultures were grown at 37° C. for 18-24 hours in a shaker (200 rpm). For growth in the biofilm reactor, TSB media was made at a concentration of 6 g/L and the temperature was 23° C.

Biofilm Reactor Method
Reactor Preparation:

Autoclaved stainless steel coupons (5 mm diameter) were rinsed twice with de-ionized water and placed into the wells of the biofilm reactor with a forceps. The tubing was then assembled and attached to the reactor vessel and autoclaved. Silicone tubing was used for the effluent port attachments (⅛"×¼", VWR International, Radnor, Pa.) and the influent port attachments (MASTERFLEX L/S 14 tubing, Cole-Parmer Instrument Co., Vernon Hills, Ill.). This is the correct size tubing for the inlet and outlet adaptors of the reactor, and also enabled the low flow rate that was desired for the system. A glass flow break was added to the system upstream from the peristaltic pump. Glass flasks (4 L) were used for nutrient supply and waste. TSB medium (6 g/L) was autoclaved in 2 L volumes and added to the sterilized glass flask used for nutrient supply. The waste flask was attached to a vacuum line in order to efficiently pull the waste media from the reactor. The system was set up inside of a biological safety hood with controlled airflow to minimize contamination.

Reactor Inoculation:

A 5 mL culture of P. aeruginosa (ATCC 15442) was inoculated with an isolated colony from trypticase soy agar (TSA). The 5 mL culture was incubated overnight at 37° C. and 200 rpm for 18-24 hours, and then diluted 1:10 into fresh TSB media. The tubing on both the inlet and outlet ports of the reactor was clamped off and 4 mL of the diluted culture was added to each test channel in the reactor. The inoculated system was incubated at 23° C. for four hours to allow the cells to adhere to the surface.

Continuous Flow Phase:

The clamps were then removed from the tubing and the reactor was set to an angle by adding a 5 mm spacer underneath the inlet side of the reactor. The pump used in this study (MASTERFLEX Pump 3, Cole-Parmer Instrument Co., Vernon Hills, Ill.) was fitted with an EASY LOAD II pump head (Cole-Parmer Instrument Co., Vernon Hills, Ill.). The pump speed was set at level 1, which resulted in a flow rate of approximately 0.7 mL/min. The continuous flow system was then run for 24 hours. If the biofilm needed to be grown for a longer period of time (48-72 hours), the waste was removed and sterile media was added to the feed flask every 24 hours.

Crystal Violet Assay

This method was adapted from a previous method (O'Toole G A, 2011, J. Vis. Exp. (47), e2437). Briefly, discs were transferred to a round bottom 96-well plate and washed with 160 μL of sterile PBS (pH 7.2) using a multichannel pipette. 150 μL of crystal violet (0.1%) was then added to each well. Discs were soaked in crystal violet for 10-15 minutes, and washed three times with 160 μL of PBS. The discs were then transferred to clean wells and washed one final time with 160 μL of PBS. 160 μL of glacial acetic acid (30%) was then added to each of the wells and incubated at room temperature for 10-15 minutes. Following this incubation period, the acetic acid solution was pipetted up and down two times and transferred to clean wells of a 96 well flat-bottom plate. Absorbance was read at 550 nm using a plate reader (BioTek Instruments, Inc., Winooski, Vt.).

XTT Assay

Following treatment of the discs, discs were transferred to a round bottom 96-well plate and washed with 160 μL of sterile PBS (pH 7.2). 2,3-Bis-(2-Methoxy-4-Nitro-5-Sulfophenyl)-2H-Tetrazolium-5-Carboxanilide) sodium salt (XTT) was added to warm PBS (55° C.) at a concentration of 0.8 mg/mL. This solution was vortexed and centrifuged for one minute to pellet the insoluble material. Menadione was added to DMSO at a concentration of 0.2 mg/mL. 25 μL of the XTT solution, 1 μL of the menadione solution, and 74 μL PBS were added to each well of the plate. The plate was incubated in the dark for a minimum of six hours at 37° C. Following the incubation period, the XTT solution was pipetted up and down twice and transferred to a new microtiter plate. The absorbance was then read at 450 nm using a plate reader (BioTek Instruments, Inc., Winooski, Vt.).

CFU Enumeration

Following treatment of the discs, the discs were transferred to a round bottom 96-well plate and washed with sterile PBS (pH 7.2). 150 μL of sterile PBS was added to each well that contained a disc. The plate was then sealed inside of a plastic bag, and placed in a water bath sonicator (sonicated on high for 30±5 minutes). A serial 10-fold dilution of each disc was then carried out in additional 96-well microtiter plates. After sonication, the content of each well was pipetted up and down two times. Then, 100 μL from each well containing a disc was transferred to the top row of a sterile flat-bottom 96-well microtiter plate. 180 μL of sterile PBS was added to each well in rows B-H of the plate. The transferred 100 μL samples were then serial diluted ($10^0$-$10^{-7}$) by transferring 20 μL from each well into the next using a multichannel pipette. Each well was mixed by pipetting two times and swirling the pipette tips in the well a total of ten revolutions. Fresh pipette tips were used for each subsequent transfer. The contents of each dilution were then spot plated on TSA using a multichannel pipette by first mixing each well and spotting 10 μL of the sample onto the TSA. Plates were incubated at 35° C.±2° C. for 16-18 hours. This method was adapted from the MBEC ASTM method (ASTM E2799-12).

Calculation of CFU/Disc:

$$\mathrm{Log}_{10}(CFU/\mathrm{disc}) = \mathrm{Log}_{10}[(A/B)(C)(D)]$$

Where:
A=CFU counted in the spot
B=Volume plated
C=Well volume
D=Dilution

Reynolds Number Calculation:

Calculation of the Reynolds number for the biofilm reactor was based on an equation developed for fluid flow through an inclined plane channel (Bird et al, 2002, Transport Phenomena, $2^{nd}$ edition. John Wiley and Sons, New York). The calculations were based on the bulk fluid being water at 20° C. The fluid flow was determined to be 0.7 mL $min^{-1}$. The fluid thickness was determined to be 1.2 mm based on the flow rate and the geometry of the channel.

Statistical Analysis

The data generated from the crystal violet assay, XTT assay, and CFU enumeration was statistically analyzed using a one-way ANOVA test. The results were generated with 3 degrees of freedom between groups, and 28 degrees of freedom within groups for the comparison of the channels. For the comparison of the rows, the results were generated with 7 degrees of freedom between groups, and 28 degrees of freedom within groups.

Example 2

Bacterial Strains and Plasmids

The bacterial strains and plasmids used in this study are listed in Table 2. *Lactococcus lactis* was cultured statically at 30±2° C. in M17 broth (Oxoid Ltd. Basingstoke, UK) supplemented with 0.5% (w/v) glucose. *Lactobacillus plantarum* was cultured statically at 37° C. in MRS broth (Oxoid Ltd. Basingstoke, UK). *Pseudomonas aeruginosa* strains were propagated at 37° C. with 200 rpm shaking in LB broth for routine growth. *Escherichia coli* DH5a was cultured at 37° C. with 200 rpm shaking in LB broth. Agar plates were made by adding 1.5% (w/v) agar to the broth media. For maintenance of plasmids, erythromycin (Em) was added to the growth media of *E. coli* and lactic acid bacterium strain at a concentration of 150 µg/mL and 6 µg/mL respectively.

TABLE 2

Strains and plasmids

| Strain | Description | Source and/or reference |
|---|---|---|
| *E. coli* DH5α | Host for cloning: F-80dlacZ M15 (lacZYA-argF) U169 recA1 endA1hsdRl7(rk−, mk+) phoAsupE44-thi-1 gyrA96 relA1 | Saltikov and Newman, 2003 |
| *L. plantarum* ATCC 14917 | Wild Type | ATCC bacteriology collection |
| *L. plantarum* WCFS1 | Wild Type | Kindly provided by Dr. Juan Borrero at the University of Minnesota |
| *P. aeruginosa* NH57388A | Stable mucoid CF mouse sputum isolate, hyperproducing alginate, functional AHL-based QS, mutation in mucA. | Kindly provide by Dr. Bryan Williams at the University of Minnesota |
| *P. aeruginosa* PAO1 ΔalgD | Alginate knockout strain | Kindly provided by Dr. Katharina Ribbeck at the Massachusetts Institute of Technology |
| *P. aeruginosa* PAO26 | Mucoid clinical isolate from cystic fibrosis patient | Kindly provide by Dr. Bryan Williams at the University of Minnesota |
| *L. lactis* subsp. *cremoris* NZ9000 | Plasmid-free strain, derivative of *L. lactis* MG1363; pepN::nisRK, non bacteriocin producer; EntA$^r$ | Kindly provided by Dr. Juan Borrero at the University of Minnesota |

| Plasmid | Description | Source and/or reference |
|---|---|---|
| pMSP3545 | Em$^r$; inducible expression vector carrying the nisA promoter and the nisR and nisK genes | Kindly provided by Dr. Juan Borrero at the University of Minnesota |
| pMG36e | Em$^r$; p32 constitutive promoter | Kindly provided by Dr. Juan Borrero at the University of Minnesota |
| pUC57-algscFv | Amp$^r$; pUC57 containing the alginate scFv (Alginate binding antibody variable region with linker peptide) synthesized by GenScript | GenScript (Piscataway, NJ) |
| pDR111-GFPsp | Amp$^r$; pDR111 containing the GFPsp gene optimized for expression in gram positive bacteria | Kindly provided by Dr. Claudia Schmidt-Dannert at the University of Minnesota |
| pJE1 | Em$^r$; pMSP3545 containing the signal peptide sequence (cloned from *L. plantarum* 14917) | This study |
| pJE2 | Em$^r$; pJE2 containing alginate scFv (synthesized | This study |

TABLE 2-continued

Strains and plasmids

| | | |
|---|---|---|
| | by GenScript) and anchor peptide (cloned from *L. plantarum* 14917) | |
| pJEGFPsp | Em$^r$; pMSP3545 containing the GFPsp gene (cloned from pDR111-GFPsp) | This study |
| pJE7 | Em$^r$; pJEGFPsp containing the binding cassette from pJE2 with a RBS site in front of the cassette | This study |

Basic Genetic Techniques and Enzymes

Qiagen kits were used for all purification of genomic DNA, PCR products, and plasmids (QIAGEN, Hilden, Germany). Restriction enzymes, T4 DNA ligase, Taq polymerase, and Antarctic phosphatase were purchased from New England Biolabs, Inc. (Ipswich, Mass.). Taq polymerase (New England Biolabs, Inc., Ipswich, Mass.) was used for colony PCR, and TaKaRa Ex Taq DNA polymerase (Clontech Laboratories, Inc., Mountain View, Calif.) was used for PCR amplification. *E. coli* cells were made competent according to standard protocols with some adaptations (Sambrook J and Russell D W, 2001, Molecular Cloning: A Laboratory Manual 3$^{rd}$ edition, Cold Spring Harbor Laboratory Press), and lactic acid bacteria strains were made electrocompetent and transformed using a GENE PULSER electroporation system (Bio-Rad Laboratories, Inc., Hercules, Calif.) as described previously (Aukrust et al., 1995, Transformation of *Lactobacillus* by Electroporation. In Electroporation Protocols for Microorganisms, J. A. Nickoloff, ed., Humana Press, pp. 201-208). Primers were purchased and DNA sequencing was performed at the University of Minnesota Biomedical Genomics Center (Minneapolis, Minn.).

Construction of Plasmids

Construction of the Binding Cassette

Primers and plasmids used in this study are listed in Table 3.

The design for the binding cassette was based on previous studies (Fredriksen et al., 2010, *Appl. Environ. Micro.* 76(21):7359-7362), but the specific construct for this work was developed during this project. The binding cassette, which included a signal peptide (Sp), an Alginate binding scFv (algscFv), and an anchor peptide (Anchor) were PCR amplified and joined together via Gibson assembly. The signal peptide and the anchor peptide were obtained from *L. plantarum* ATCC 14917 genomic DNA using PrimF-Sp (SphI)6-9 and PrimR-Sp(SpeI)6-9 for the signal peptide, and PrimF-Anchor and PrimR-Anchor(SpeI)pMSP for amplification of the anchor peptide sequence. The anchor peptide is a truncated version of 1p_2578, accession no. YP_004890243. The algscFv binding protein sequence design included the heavy and light chain of the F429 mAb (F429 IGHV-D-J accession no. AY626664.1, and F429 IGLV-J accession no. AY626662) as previously described (Pier et al., 2004, *J Immunol* 173(9), 5671-5678). The heavy and light chains from this mAb were fused together with a linker peptide sequence (GGGGS)$_3$ (SEQ ID NO:9) in order to enable proper folding and display of the scFv. The algscFv was codon-optimized for expression in *Lactobacillus* and synthesized by GenScript (Piscataway, N.J.). GenScript originally sent this algscFv gene product in pUC57. PrimF-OptalgscFv and PrimR-OptalgscFv were used to amplify the algscFv gene from pUC57. The binding construct was cloned into pMSP3545 and regulated by the pNisA nisin inducible promoter.

TABLE 3

Primer sequences

| Primer | Nucleotide sequence (5'-3') |
|---|---|
| PrimF-Sp(SphI) 6-9 | TTA GCATGC TATA AGGAGG CACTCAACATGGGGAGGAG CGTATGCGAAGA (SEQ ID NO: 1) |
| PrimR-Sp(SpeI) 6-9 | TAAGTT ACTAGT TCAAGCACGACGGCGATAACC (SEQ ID NO: 2) |
| PrimF-OptalgscFv | CACATGCTAAAGAAATCTTCTAGACAGTTACAGTTACAA GAAAGTG (SEQ ID NO: 3) |
| PrimR-OptalgscFv | GGCCATGGAACTGTCAATTTCGTGCC (SEQ ID NO: 4) |
| PrimF-Anchor | TTGACAGTTCCATGGCCGGTCACTGAACCAGGA (SEQ ID NO: 5) |
| PrimR-Anchor(SpeI)pMSP | TAAGTT ACTAGT TCAAGCACGACGGCGATAACC (SEQ ID NO: 6) |
| PrimF-GFPsp(NcoI) | CATGCATGC CCATGG TTTCTAAAGGTGAAGAATTG (SEQ ID NO: 7) |
| PrimR-GFPsp(SphI) | CCGG GCATGC TTATTTATACAATTCATCCATACCATG (SEQ ID NO: 8) |

$^a$ Restriction enzyme cleavage sites are underlined in the primers; RBS site shown in bold Construction of pJEGFPsp and pJE7

The GFPsp gene was provided by Dr. Claudia Schmidt-Dannert (St. Paul, Minn.). The GFPsp gene was amplified from the pDR111-GFPsp plasmid using PrimF-GFPsp (NcoI) and PrimR-GFPsp(SphI). This PCR product was cloned into pMSP3545 using the NcoI and SphI restriction enzyme sites, which yielded the pJEGFPsp plasmid. pJE7 was obtained by amplifying the binding cassette with PrimF-sp(SphI)6-9 and PrimR-Anchor(SpeI) and cloning this PCR product into the pJEGFPsp using the sphI and speI site, which yielded the pJE7 plasmid. The PrimF-sp(SphI)6-9 primer also contained a RBS binding site that was identical to the RBS site that is found in the pNisA promoter region.

Characterization of Nisin Induction

Overnight cultures of *L. lactis* (pJEGFPsp or pJE7) cells were diluted 1:100 in 5 mL of M17 (Oxoid Ltd. Basingstoke, UK)+glucose (0.5%) supplemented with 6 µg/mL erythromycin. After two hours of growth at 32° C., the cultures were induced with various concentrations of nisin (0-40 ng/mL). Optical density measurements (600 nm) were recorded every hour for seven hours, and GFP expression was measured using a fluorescent plate reader.

Protein Characterization

Cultures were started by adding 100 µL of an overnight culture to sterile M17 (Oxoid Ltd. Basingstoke, UK)+ glucose (0.5%) (10 mL) supplemented with 6 µg/mL erythromycin. After two hours of growth at 32° C., the cultures were induced with 10 ng/mL nisin. Cells were harvested by centrifugation at 4,000 rpm for 10 minutes after an additional four hours of growth at 32° C. The supernatant was removed and the pellet was re-suspended in 10 mL of PBS (pH 7.2). Cells were then sonicated with a sonicator (BRANSON 250, Branson Ultrasonics, Danbury, Conn.) set at an output power of 6 for eight minutes. Sonication pulses were set to sonicate 30% of the total time—i.e., for every three seconds of sonication there was a seven second intermission time period. Following sonication, the lysed cells were centrifuged at 10,000×g for 10 minutes to remove the cell debris. The pellet was re-suspended in 100 µL of PBS, and the supernatant was centrifuged at 100,000×g for 30 minutes. The resulting pellet, which contained the cellular membrane components, was re-suspended in 30 µL of PBS. Protein concentrations were determined according to the Coomassie Plus (Bradford) Assay Kit (ThermoFisher Scientific, Rockford, Ill.).

Samples were treated with BOLT (Life Technologies, Carlsbad, Calif.) non-reducing sample buffer and incubated at 70° C. for 10 minutes. To visualize the expression and the location of the binding cassette product and GFP, the samples were separated on a 10% Bis-Tris polyacrylamide gel. Gels were then stained with Coomassie for two hours followed by a minimum of three hours of de-staining with 50% methanol and 10% glacial acetic acid.

Quantification of Alginate

Alginate was precipitated from 1 mL aliquots taken from 5 mL *P. aeruginosa* cultures that were grown at 37° C. for 48 hours. The 1 mL aliquots were centrifuged at 23,000×g for 30 minutes at 4° C. The resulting pellet was discarded, and the supernatant was added to 3 mL of 99% ice-cold ethanol. The precipitate was centrifuged at 5,000×g for five minutes at 4° C., and the pellet was dissolved in 0.9% saline (Hoffmann et al., 2005, *Infect. Immun.* 73:2504-2514). Quantification of alginate was then carried out according to the carbazole-borate method as previously described (Knutson C A and Jeanes A, 1968, *Anal Chem* 24:470-481) with some modifications. Briefly, 190 µL of boric acid (100 mM) was added to the wells of a 96-well plate. An aliquot (30 µL) of the purified alginate sample was then added to the wells with boric acid and mixed by pipetting up and down twice. Carbazole solution (30 µL, 0.1% in ethanol) was added to the wells and mixed as before. The plate was then sealed and placed in a 55° C. incubator for 40 minutes. The resulting absorbance values were read at 530 nm. A standard curve based on known concentrations of pure alginate (3.125-50 µg/mL, final concentration in wells) was used to determine the concentration of the unknown samples.

Characterization of Binding to *P. aeruginosa* Biofilms

*P. aeruginosa* Growth in Biofilm Reactor

*P. aeruginosa* NH57388A and *P. aeruginosa* PAO26, was grown in LB (20 g/L)+glycerol (1%) overnight at 37° C. and 200 rpm shaking. LB media is commonly used for *Pseudomonas* alginate production, and glycerol has been found to promote alginate production (Wingender et al., 2001; Hoffman et al., 2005). This culture was then diluted 1:10 in sterile LB (20 g/L)+glycerol (1%). The channels of the biofilm reactor were inoculated with 4 mL of the diluted culture and held statically for four hours at room temperature. Growth in the reactor was then carried out over a period of six days (48 hours of flow at 0.7 ml min$^{-1}$, then held static for 48 hours, followed by an additional 24 hours of flow) with LB (6 g/L)+glycerol (1%). The long growth period was used due to the slow growth of *P. aeruginosa* NH57388A. Sample discs were pulled from the reactor throughout this cycle to quantify the biofilm growth using the crystal violet assay. Following the six days of growth in the biofilm reactor, discs were removed and transferred to a 96-well plate.

*P. aeruginosa* Growth in 96-Well Plate

*P. aeruginosa* NH57388A, was grown in LB (20 g/L)+ glycerol (1%) overnight at 37° C. and 200 rpm shaking. This culture was then diluted 1:10 in sterile LB (20 g/L)+glycerol (1%). 150 µL of this diluted culture was then added to the wells of a 96-well plate and incubated for 72 hours at 35±2° C. and 100 rpm shaking. After 72 hours, the media was removed from the wells and sterile LB (20 g/L)+glycerol (1%) was added to the wells. This was done to supply the established biofilm with fresh media nutrients. The plate was incubated for an additional 24 hours. *P. aeruginosa* (PAO1 ΔalgD) biofilms were grown as described for PA NH57388A except that the biofilm was grown for 24 hours. This difference in biofilm growth time was due to the difference in biofilm growth rates of these *P. aeruginosa* strains. After biofilm growth, the spent media was removed from the wells and the wells were washed once with sterile PBS (pH 7.2) to remove unattached planktonic cells.

Preparation of *L. lactis* Cells for Binding Studies

*L. lactis* cells were prepared and induced as described in the 'Characterization of nisin induction' section, above. The induced cultures were then diluted 1:3 in sterile M17+ glucose broth supplemented with 6 µg/mL erythromycin and 10 ng/mL nisin. This diluted cell culture was then added to the wells of a 96-well plate that either had the biofilm grown on the walls of the wells, or the biofilm grown on the steel discs using the biofilm reactor. The induced *L. lactis* cells were exposed to the biofilm for a period of 3.5 hours at room temperature. Discs and wells were washed (once to six times, depending on the assay performed) with sterile PBS (pH 7.2) to remove unattached cells. The plate was then sonicated in a water bath on high for 30 min to detach the biofilm from the surface. The contents of the wells were then mixed using a multichannel pipette by pipetting up and down twice and swirling the pipette tips for 10 revolutions.

Fluorescence Microscopy

Steel discs treated as described in the previous section (washed five times with PBS) were viewed under a conventional epifluorescence microscope (Olympus BX51, Center Valley, Pa.) with an Xcite light source. An FITC filter source was used, and the study was performed in duplicate. Multiple images were taken of each surface, and representative images were chosen for display in the results section.

Quantitative Binding Assay

After L. lactis exposure to PA biofilms and washing (as described above), the plate was sonicated in a water bath on high for 30 minutes to detach the biofilm from the surface. The contents of the wells were then mixed using a multi-channel pipette by pipetting up and down 2× and swirling the pipette tips for 10 revolutions. For wells that contained the steel discs, aliquots of the re-suspended cell solution were transferred to clean wells for analysis. Relative fluorescent units were measured using a fluorescent plate reader (Top read, Excitation 485 nm/Emission 528 nm, sensitivity 70). To determine the percentage of fluorescence retained after washing, the fluorescence measured for each test well was divided by the average initial fluorescence measurement for each GFP producing strain of L. lactis.

Preliminary Testing of Lactic Acid Bacteria Strains Against P. aeruginosa Biofilms Lactobacillus sp. Supernatant and Cell Culture Study P. aeruginosa (PAO26) biofilms were grown at 37° C. in TSB for 24 hours in a 96-well plate at 90 rpm. The planktonic PAO26 culture was removed from the wells of the 96-well plate. Overnight cultures of L. plantarum strains (WCFS1, NC8, 14917, and 10241) were grown at 37° C. in MRS. To obtain the supernatants, cultures were centrifuged at 4000 rpm for 10 minutes. A portion of each supernatant was pH neutralized (pH 7) with NaOH. The un-neutralized supernatant from each sample was acidic (pH~3.7). Following neutralization, the supernatants were filter sterilized. The supernatants were added to the wells containing the biofilms in triplicate with final concentrations ranging from 5%-25% (total well volume was 160 µL). The base media in the wells was TSB media. The supernatants were exposed to the biofilms for 18-24 hours at 37° C. For the cell culture study, a 2 µL aliquot from each culture was used to inoculate the wells containing the PAO26 biofilms and fresh TSB (performed in quadruplicates). The plate was then incubated for an additional 24 hours at 37° C. Following the supernatant and cell culture treatments, the crystal violet assay was performed for each test.

L. plantarum WCFS1 and Tobramycin Study Against P. aeruginosa Biofilms

P. aeruginosa (PAO26) biofilms were grown at 37° C. in TSB for 24 hours in a 96-well plate at 90 rpm. The planktonic PAO26 culture was removed from the wells of the 96-well plate. Overnight cultures of L. plantarum WCFS1 was grown at 37° C. in MRS. An aliquot (5 µL) of the WCFS1 cell culture was then added to the wells containing the biofilms and fresh TSB. The plate was incubated overnight, and the following day wells were treated with tobramycin (0-360 µg/mL) for an additional 24 hours. Following the treatments, CFU enumeration was performed as described in the materials and methods section of chapter 2 with one exception. TSB plates were supplemented with 5 µg/mL chloramphenicol to inhibit the growth of L. plantarum (WCFS1). Prior to performing this test, P. aeruginosa verified to be resistant to this concentration of chloramphenicol.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A fusion polypeptide comprising:
   an anchor domain comprising:
      an LPXTG (SEQ ID NO:10) motif; or
      an LPQTXE (SEQ ID NO:11) motif; and
   a binding domain comprising at least a portion of a polypeptide that specifically binds to a component of a target biofilm, the biofilm component comprising alginate.

2. The fusion polypeptide of claim 1 wherein the target biofilm comprises *Pseudomonas aeruginosa*.

3. The fusion polypeptide of claim 1 wherein the binding domain comprises at least a portion of an antibody effective to specifically bind to the component of the target biofilm.

4. The fusion polypeptide of claim 3 wherein the binding domain comprises a scFv.

* * * * *